(12) United States Patent
Schabbach et al.

(10) Patent No.: US 11,642,468 B2
(45) Date of Patent: May 9, 2023

(54) MEDICAMENT INJECTION DEVICE WITH ROTARY ENCODER

(71) Applicant: SANOFI, Paris (FR)

(72) Inventors: Michael Schabbach, Frankfurt am Main (DE); Anthony Paul Morris, Warwick (GB); Ronald Antony Smith, Warwick (GB); Brian Charles Molyneux, Warwick (GB); Paul Richard Draper, Warwick (GB); Craig Ashley Mason, Warwick (GB); Oliver Charles Gazeley, Warwick (GB); Daniel Edward Clark, Warwick (GB); David Aubrey Plumptre, Warwick (GB); Aidan Michael O'Hare, Warwick (GB); Richard James Thomas, Warwick (GB); Felix Kramer, Wil (CH); Beat Wyss, Wil (CH); Philipp Muller, Wil (CH)

(73) Assignee: Sanofi, Paris (FR)

( * ) Notice: Subject to any disclaimer, the term of this patent is extended or adjusted under 35 U.S.C. 154(b) by 285 days.

(21) Appl. No.: 16/766,144

(22) PCT Filed: Nov. 23, 2018

(86) PCT No.: PCT/EP2018/082438
§ 371 (c)(1),
(2) Date: May 21, 2020

(87) PCT Pub. No.: WO2019/101962
PCT Pub. Date: May 31, 2019

(65) Prior Publication Data
US 2020/0360614 A1    Nov. 19, 2020

(30) Foreign Application Priority Data
Nov. 23, 2017 (EP) .................................. 17306626

(51) Int. Cl.
| A61M 5/315 | (2006.01) |
| A61M 5/31 | (2006.01) |
| A61M 5/32 | (2006.01) |

(52) U.S. Cl.
CPC ...... A61M 5/3155 (2013.01); A61M 5/31551 (2013.01); A61M 5/3202 (2013.01);
(Continued)

(58) Field of Classification Search
CPC .......... A61M 5/31551; A61M 5/31568; A61M 2005/3126; A61M 2005/2488; A61M 2205/3306; A61M 2205/52; G01D 5/3473
See application file for complete search history.

(56) References Cited

U.S. PATENT DOCUMENTS

| 3,967,177 A | 6/1976 | Scholten et al. |
| 4,707,128 A | 11/1987 | Coles |

(Continued)

FOREIGN PATENT DOCUMENTS

| CN | 102971701 | 3/2013 |
| CN | 104902944 | 9/2015 |

(Continued)

OTHER PUBLICATIONS

PCT International Preliminary Report on Patentability in Application No. PCT/EP2018/082438, dated May 26, 2020, 8 pages.
(Continued)

*Primary Examiner* — Tasnim Mehjabin Ahmed
(74) *Attorney, Agent, or Firm* — Fish & Richardson P.C.

(57) ABSTRACT

The present disclosure relates to medicament injection devices. An injection device includes: a movable dosage programming component comprising a rotary encoder system having a predefined angular periodicity, a sensor arrangement including a first optical sensor configured to detect movement of the movable dosage programming com-
(Continued)

ponent relative to the sensor arrangement during dosing of a medicament, wherein the first optical sensor is configured to operate in a strobe-sampling mode at a first frequency, a second optical sensor configured to detect movement of the rotary encoder system relative to the second optical sensor wherein the second optical sensor is configured to operate in a strobe-sampling mode at a second frequency lower than the first frequency, and a processor arrangement configured to, based on the detected movement, determine a medicament dosage administered by the injection device.

20 Claims, 27 Drawing Sheets

(52) U.S. Cl.
CPC .............. *A61M 2005/3126* (2013.01); *A61M 2205/3306* (2013.01); *A61M 2205/3584* (2013.01); *A61M 2205/52* (2013.01); *A61M 2205/581* (2013.01); *A61M 2205/8212* (2013.01)

(56) References Cited

U.S. PATENT DOCUMENTS

| | | | |
|---|---|---|---|
| 5,130,710 | A | 7/1992 | Salazar |
| 6,287,283 | B1 | 9/2001 | Ljunggreen et al. |
| 6,585,698 | B1 | 7/2003 | Packman et al. |
| 6,799,090 | B2 | 9/2004 | Farina et al. |
| 7,008,399 | B2 | 3/2006 | Larsen et al. |
| 7,138,806 | B2 | 11/2006 | Gafner et al. |
| 7,347,200 | B2 | 3/2008 | Jones et al. |
| 7,498,563 | B2 | 3/2009 | Mandro et al. |
| 7,749,186 | B2 | 7/2010 | Kohlbrenner et al. |
| 7,988,660 | B2 | 8/2011 | Byland et al. |
| 8,049,519 | B2 | 11/2011 | Nielsen et al. |
| 8,052,655 | B2 | 11/2011 | Moller et al. |
| 8,128,604 | B2 | 3/2012 | Yeandel et al. |
| 8,197,449 | B2 | 6/2012 | Nielsen et al. |
| 8,221,356 | B2 | 7/2012 | Enggaard et al. |
| 8,529,520 | B2 | 9/2013 | Daniel |
| 8,556,865 | B2 | 10/2013 | Krulevitch et al. |
| 8,560,271 | B2 | 10/2013 | Koehler et al. |
| 8,708,957 | B2 | 4/2014 | Jespersen et al. |
| 9,152,829 | B2 | 10/2015 | Day et al. |
| 9,186,465 | B2 | 11/2015 | Jorgensen et al. |
| 9,192,728 | B2 | 11/2015 | Gilmore et al. |
| 9,233,210 | B2 | 1/2016 | Bock et al. |
| 9,289,559 | B2 | 3/2016 | Pedersen et al. |
| 9,314,573 | B2 | 4/2016 | Nielsen et al. |
| 9,526,842 | B2 | 12/2016 | Oh et al. |
| 9,545,482 | B2 | 1/2017 | Binier |
| 9,623,188 | B2 | 4/2017 | Nielsen et al. |
| 9,649,448 | B2 | 5/2017 | Madsen |
| 9,672,328 | B2 | 6/2017 | Saint et al. |
| 9,734,302 | B2 | 8/2017 | Nielsen et al. |
| 9,750,886 | B2 | 9/2017 | Plambech et al. |
| 9,775,957 | B2 | 10/2017 | Despa et al. |
| 9,833,576 | B2 | 12/2017 | Windum et al. |
| 10,086,147 | B2 | 10/2018 | Despa et al. |
| 10,105,489 | B2 | 10/2018 | Edwards et al. |
| 10,117,999 | B2 | 11/2018 | Andersen |
| 10,155,090 | B2 | 12/2018 | Larsen et al. |
| 10,159,797 | B2 | 12/2018 | Andersen et al. |
| 10,183,119 | B2 | 1/2019 | Andersen et al. |
| 10,201,664 | B2 | 2/2019 | Madsen et al. |
| 10,226,577 | B2 | 3/2019 | Radmer et al. |
| 10,258,745 | B2 | 4/2019 | Despa et al. |
| 10,269,266 | B2 | 4/2019 | Rios et al. |
| 10,332,699 | B2 | 6/2019 | Radmer et al. |
| 10,376,644 | B2 | 8/2019 | Krusell et al. |
| 10,383,996 | B2 | 8/2019 | Miller et al. |
| 10,384,013 | B2 | 8/2019 | Krusell et al. |
| 10,398,852 | B2 | 9/2019 | Taylor et al. |
| 10,617,827 | B2 | 4/2020 | Hautaviita et al. |
| 10,653,852 | B2 | 5/2020 | Bauss et al. |
| 10,668,220 | B2 | 6/2020 | Hautaviita et al. |
| 10,688,255 | B2 | 6/2020 | Mirov et al. |
| 10,695,504 | B2 | 6/2020 | Nielsen et al. |
| 2014/0194825 | A1* | 7/2014 | Nielsen ................. G16H 15/00 604/207 |
| 2015/0343152 | A1* | 12/2015 | Butler ............... A61M 5/31585 604/207 |
| 2016/0287804 | A1 | 10/2016 | Madsen et al. |
| 2016/0287807 | A1 | 10/2016 | Madsen et al. |
| 2016/0378951 | A1* | 12/2016 | Gofman ............ A61M 5/31528 604/504 |
| 2017/0115395 | A1 | 4/2017 | Grauer et al. |
| 2017/0338864 | A1 | 11/2017 | Rolsted et al. |
| 2018/0250473 | A1 | 9/2018 | Ganzitti |
| 2018/0369494 | A1 | 12/2018 | Grubbe |
| 2019/0001060 | A1 | 1/2019 | Gylleby et al. |
| 2019/0038843 | A1 | 2/2019 | Byerly et al. |
| 2019/0151559 | A1 | 5/2019 | Byerly et al. |
| 2019/0160229 | A1 | 5/2019 | Alagia et al. |
| 2020/0023137 | A1 | 1/2020 | Byerly et al. |
| 2020/0114087 | A1 | 4/2020 | Bauer et al. |
| 2020/0147318 | A1 | 5/2020 | Antonelli et al. |
| 2020/0171246 | A1* | 6/2020 | Byerly .............. A61M 5/31535 |

FOREIGN PATENT DOCUMENTS

| | | |
|---|---|---|
| CN | 104918648 | 9/2015 |
| CN | 104936640 | 9/2015 |
| JP | 2004-347382 | 12/2004 |
| JP | 2014-520584 | 8/2014 |
| JP | 2017-507735 | 3/2017 |
| WO | WO 2011/160079 | 12/2011 |
| WO | WO 2013/004844 | 1/2013 |
| WO | WO 2014/033195 | 3/2014 |
| WO | WO 2014/108494 | 7/2014 |
| WO | WO 2014/111339 | 7/2014 |
| WO | WO 2014/111340 | 7/2014 |
| WO | WO 2014/111341 | 7/2014 |
| WO | WO 2015/138093 | 9/2015 |
| WO | WO 2016/050902 | 4/2016 |
| WO | WO 2018/013419 | 1/2018 |
| WO | WO 2018/141571 | 8/2018 |
| WO | WO 2019/001919 | 1/2019 |
| WO | WO 2019/040118 | 2/2019 |
| WO | WO 2019/040313 | 2/2019 |
| WO | WO 2019/046053 | 3/2019 |
| WO | WO 2019/053179 | 3/2019 |
| WO | WO 2019/057916 | 3/2019 |

OTHER PUBLICATIONS

PCT International Search Report and Written Opinion in Application No. PCT/EP2018/082438, dated Feb. 15, 2019, 11 pages.

\* cited by examiner

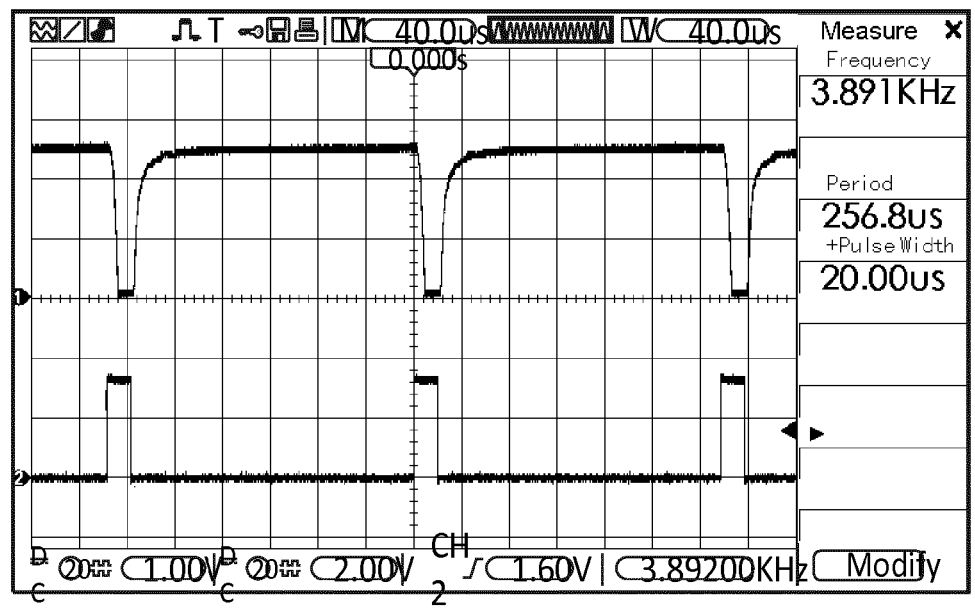
FIG. 19A
FIG. 19B
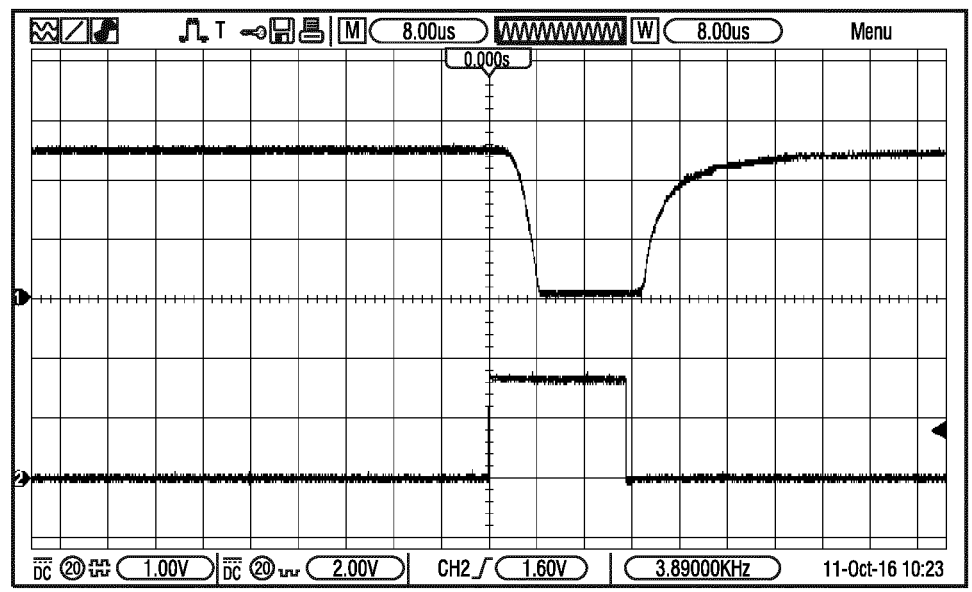

MEDICAMENT INJECTION DEVICE WITH ROTARY ENCODER

CROSS REFERENCE TO RELATED APPLICATIONS

The present application is the national stage entry of International Patent Application No. PCT/EP2018/082438, filed on Nov. 23, 2018, and claims priority to Application No. EP 17306626.7, filed on Nov. 23, 2017, the disclosures of which are incorporated herein by reference.

TECHNICAL FIELD

The present disclosure is generally to medicament injection devices.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose.

SUMMARY

According to a first aspect, this disclosure describes an injection device comprising: a movable dosage programming component comprising a rotary encoder system having a predefined angular periodicity; a sensor arrangement comprising a first optical sensor configured to detect movement of the movable dosage programming component relative to the sensor arrangement during dosing of a medicament, wherein the first optical sensor is configured to operate in a strobe-sampling mode at a first frequency, and a second optical sensor configured to detect movement of the rotary encoder system relative to the second optical sensor, wherein the second optical sensor is configured to operate in a strobe-sampling mode at a second frequency lower than the first frequency; and a processor arrangement configured to, based on said detected movement, determine a medicament dosage administered by the injection device.

The rotary encoder system may be configured to be rotatable with respect to the first optical sensor during a dialing mode of operation of the injection device.

The rotary encoder system may comprise an encoder ring comprising a plurality of substantially light reflective flags arranged circumferentially around the encoder ring in accordance with the predefined periodicity.

The encoder ring may comprise a plurality of substantially light absorbent flags arranged to alternate with the plurality of substantially light reflective flags in accordance with the predefined periodicity.

Lateral edges of the plurality of substantially light reflective flags may be inwardly inclined.

The second optical sensor may be configured to operate in a strobe-sampling mode at a second frequency lower than the first frequency.

The first and second optical sensors may have an angular offset equal to half the predefined angular periodicity, with the first and second optical sensors configured to operate in a synchronous mode of operation.

The first and second optical sensors may have an angular offset that differs from half the predefined angular periodicity, with the first and second optical sensors configured to operate in a staggered mode of operation with an offset time between sampling by the first and second optical sensors.

The angular offset may be less than half the predefined angular periodicity.

The offset time may be varied based on a relative rotational speed of rotary encoder system with respect to the first and second optical sensors.

The offset time may be decreased in response to an increase in relative rotational speed.

The injection device may further comprise an injection button and an electrical switch connected to the sensor arrangement, the electrical switch arranged to supply power to the sensor arrangement in response to actuation of the injection button.

The injection device may further comprise a cartridge containing a medicament.

According to a second aspect, this disclosure describes a module configured to be used with or applied to an injection device comprising a movable dosage programming component with a rotary encoder system, particularly an injection device as described herein, the module comprising: a sensor arrangement comprising at least one optical sensor being configured to detect movement of the movable dosage programming component of the injection device relative to the sensor arrangement during dosing of a medicament and a collimating optics being arranged between the at least one optical sensor and the movable dosage programming component; and a processor arrangement configured to, based on said detected movement, determine a medicament dosage administered by the injection device.

The collimating optics may comprise one or more of the following: one or more discrete collimating lenses; one or more light pipes.

A discrete collimating lens may be arranged between each optical sensor and each light pipe and/or between each light pipe and the movable dosage programming component.

A single discrete collimating lens may be provided for each sensor and configured to cover the transmitter and/or receiver portion of the sensor.

The single discrete lens may be a lens array covering the sensor, particularly a micro-moulded lens array.

The one or more light pipes may have the shape of a frustum, particularly with a circular or an elliptic base, According to a third aspect, this disclosure describes a method for processing signals generated by a sensor arrangement of an injection device as described above and disclosed herein or a module as described above and disclosed herein, which comprises a sensor arrangement with two optical sensors arranged with a 180° shift such that the signal of the first sensor of the two sensors and the signal of the second sensor of the two sensors are in anti-phase, the method comprising the steps of setting a high threshold and a low threshold for the signal of the first sensor and for the signal of the second sensor, respectively, and counting a unit of a dose selected with the movable dosage programming component if the signal of the second sensor passes the high threshold and thereafter passes the low threshold, and thereafter the signal of the first sensor passes the low threshold and thereafter passes the high threshold.

The step of setting a high threshold and a low threshold for the signal of the first sensor and for the signal of the second sensor, respectively, may comprise a calibration step performed during manufacturing of the module for setting the high and low thresholds, wherein the calibration step comprises passing a set of calibration geometry beneath each sensor at controlled distances for calibration, and setting the high and low thresholds such that the high threshold is always below the largest level of the respective sensor signal observed during calibration and the low threshold is always below the smallest signal level observed during calibration.

The step of setting a high threshold and a low threshold for the signal of the first sensor and for the signal of the second sensor, respectively, may comprise the steps of setting a sampling frequency for sampling the signals of both sensors to a level higher than a sampling frequency used for normal operation and sampling the signals during delivery of a dose with an injection device comprising the module, determining the magnitudes of at least two consecutive peak-throughs of the signal of each sensor, and setting the high threshold and the low threshold for each signal to a percentage of the the determined magnitudes of at least two consecutive peak-throughs if the determined magnitudes of at least two consecutive peak-throughs are within a predetermined tolerance signal range.

According to a fourth aspect, this disclosure describes a method for processing signals generated by a sensor arrangement of an injection device as described above and disclosed herein or a module as described above and disclosed herein, which comprises a sensor arrangement with two optical sensors arranged with a 180° shift such that the signal of the first sensor of the two sensors and the signal of the second sensor of the two sensors are in anti-phase, the method comprising the steps of determining of a first crossover point when the level of the signal of the second sensor becomes greater than the level of the signal of the first sensor, determining of a second crossover point when the level of the signal of the first sensor becomes greater than the level of the signal of the second sensor, and counting a unit of a dose selected upon determining the first crossover point after having determined the second crossover point.

The determining of a crossover point when the level of the signal of the one sensor becomes greater than the level of the signal of the other sensor may comprise determining that the difference of the levels of the signals of both sensors exceeds a predetermined threshold.

The method may further comprise a calibration step performed during manufacturing of the module for matching the signals of both sensors in terms of mean signal and signal amplitude, wherein for calibration a set of calibration geometry is passed beneath each sensor at controlled distance and scaling factors for mean and amplitude are applied to the second sensor to match the mean and amplitude of its signal to the mean and amplitude of the signal of the first sensor. Alternatively, the method may further comprise a calibration step performed after selecting a dose, wherein for calibration a dataset for the signals of both sensors is stored and scaling factors are retrospectively calculated from the stored dataset in order to obtain a common mean and amplitude between the signals of both sensors.

According to a fifth aspect, this disclosure describes a method for processing signals generated by a sensor arrangement of an injection device as described above and disclosed herein or a module as described above and disclosed herein, which comprises a sensor arrangement with two optical sensors arranged with a 180° shift such that the signal of the first sensor of the two sensors and the signal of the second sensor of the two sensors are in anti-phase, the method comprising the steps of determining peaks of the signals of the first sensor and the second sensor during selection of a dose, and counting a unit of a dose selected when a peak of the signal of the first sensor has been detected after a peak of the signal of the second sensor has been detected.

According to a sixth aspect, this disclosure describes an injection device comprising: a rotary encoder system having a predefined angular periodicity and an encoder ring comprising a plurality of light reflectors arranged circumferentially around the encoder ring in accordance with the predefined periodicity, wherein each light reflector is designed for total internal reflection of an incident light beam; a sensor arrangement comprising a light emitter arranged to emit a light beam directed to a light reflector of the encoder ring and two light receivers arranged to receive a light beam reflected by the light reflector of the encoder ring, wherein the sensor arrangement is configured to detect movement of the movable dosage programming component relative to the sensor arrangement during dosing of a medicament; and a processor arrangement configured to, based on said detected movement, determine a medicament dosage administered by the injection device.

Each light reflector may comprise two reflecting surfaces arranged perpendicular to each other such that an incident light beam is reflected from one reflecting surface to the other reflective surface and reflected from the other reflective surface to the light receivers.

The light reflectors may be made from a transparent material and the two reflecting surfaces of each light reflector are high-polished in order to reflect light incident on the light reflector.

Either the rotary encoder system or the sensor arrangement may be configured to be rotated during dosing of a medicament.

BRIEF DESCRIPTION OF THE FIGURES

So that the general concepts set out in the foregoing sections can be more fully understood, embodiments thereof will be described with reference to the accompanying drawings, in which:

FIG. 19A is a screenshot showing scope traces obtained from various embodiments;

FIG. 19B is a close-up view of the screenshot of FIG. 19A;

DETAILED DESCRIPTION

In the following, embodiments will be described with reference to an insulin injection device. The present disclosure is however not limited to such application and may equally well be deployed with injection devices that eject other medicaments.

Embodiments are provided in relation to injection devices, in particular to variable dose injection devices, which record and/or track data on doses delivered thereby. These data may include the size of the selected dose, the time and date of administration, the duration of the administration and the like. Features described herein include the arrangement of sensing elements, power management techniques (to facilitate small batteries) and a trigger switch arrangement to enable efficient power usage.

Certain embodiments in this document are illustrated with respect to Sanofi's AIISTAR® injection device where an injection button and grip are combined. The mechanical construction of the AIISTAR® injection device is described in detail in the international patent application WO2014/033195A1, which is incorporated herein by reference. Other injection devices with the same kinematical behaviour of the dial extension and trigger button during dose setting and dose expelling operational mode are known as, for example, the Kwikpen® device marketed by Eli Lilly and the Novopen® device marketed by Novo Nordisk. An application of the general principles to these devices therefore appears straightforward and further explanations will be omitted. However, the general principles of the present disclosure are not limited to that kinematical behaviour. Certain other embodiments may be conceived for application to Sanofi's SoloSTAR® injection device where there are separate injection button and grip components.

In the following discussion, the terms "distal", "distally" and "distal end" refer to the end of an injection device towards which a needle is provided. The terms "proximal", "proximally" and "proximal end" refer to the opposite end of the injection device towards which an injection button or dosage knob is provided.

Figure 1:
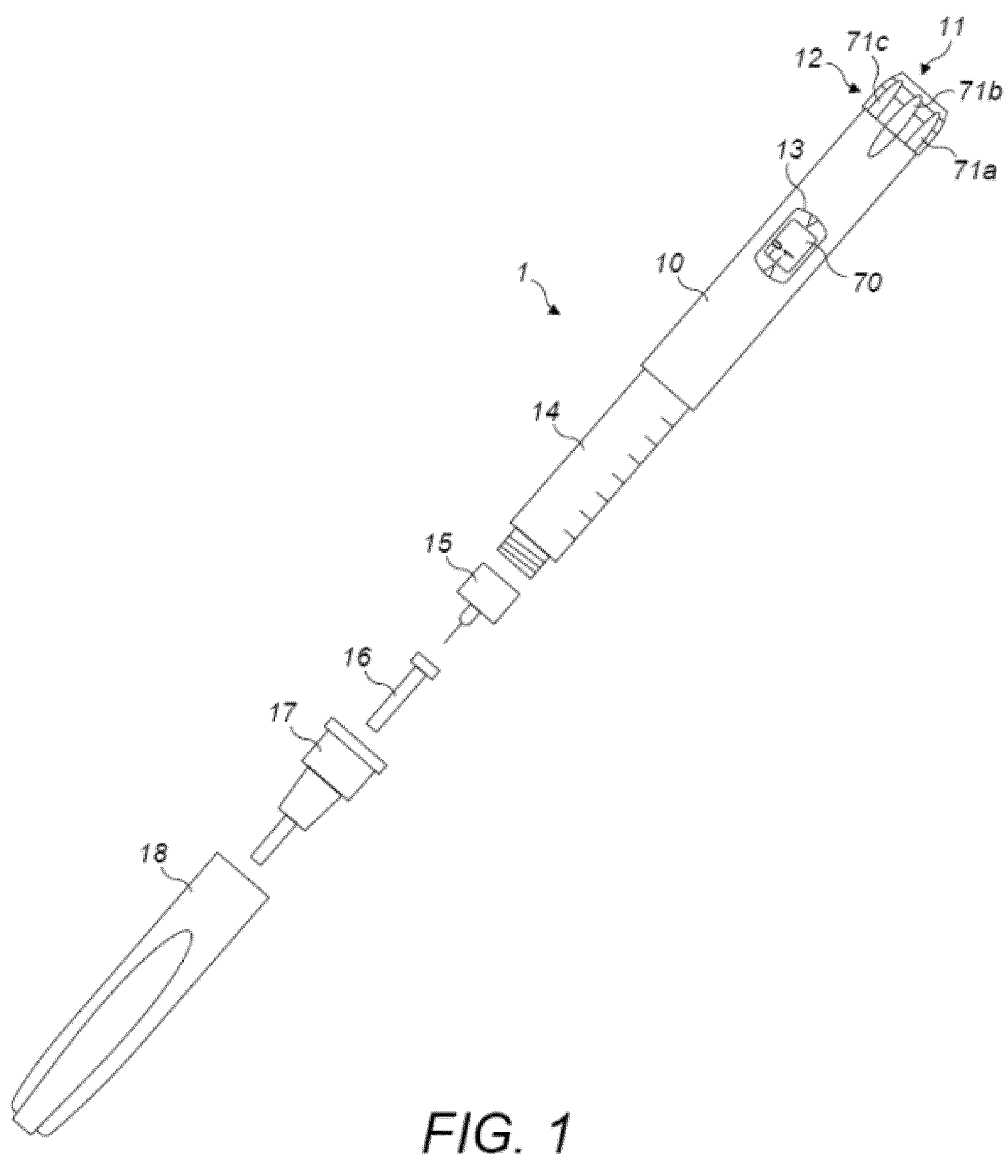
FIG. 1 shows an injection device according to a first embodiment.

FIG. 1 is an exploded view of a medicament delivery device. In this example, the medicament delivery device is an injection device 1, such as Sanofi's AIISTAR® injection pen.

The injection device 1 of FIG. 1 is a pre-filled, disposable injection pen that comprises a housing 10 and contains an insulin container 14, to which a needle 15 can be affixed. The needle is protected by an inner needle cap 16 and either an outer needle cap 17 other cap 18. An insulin dose to be ejected from injection device 1 can be programmed, or 'dialed in' by turning a dosage knob 12, and a currently programmed dose is then displayed via dosage window 13, for instance in multiples of units. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a dial sleeve 70 that is configured to move when the dosage knob 12 is turned, to provide a visual indication of a currently programmed dose. The dosage knob 12 is rotated on a helical path with respect to the housing 10 when turned during programming.

In this example, the dosage knob 12 includes one or more formations 71a, 71b, 71c to facilitate attachment of a data collection device.

The injection device 1 may be configured so that turning the dosage knob 12 causes a mechanical click sound to provide acoustical feedback to a user. The dial sleeve 70 mechanically interacts with a piston in insulin container 14. In this embodiment, the dosage knob 12 also acts as an injection button. When needle 15 is stuck into a skin portion of a patient, and then dosage knob 12 is pushed in an axial direction, the insulin dose displayed in display window 13 will be ejected from injection device 1. When the needle 15 of injection device 1 remains for a certain time in the skin portion after the dosage knob 12 is pushed, a high percentage of the dose is actually injected into the patient's body. Ejection of the insulin dose may also cause a mechanical click sound, which is however different from the sounds produced when rotating the dosage knob 12 during dialing of the dose.

In this embodiment, during delivery of the insulin dose, the dosage knob 12 is returned to its initial position in an axial movement, without rotation, while the dial sleeve 70 is rotated to return to its initial position, e.g. to display a dose of zero units.

Injection device 1 may be used for several injection processes until either the insulin container 14 is empty or the expiration date of the medicament in the injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing dosage knob 12 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

As explained above, the dosage knob 12 also functions as an injection button so that the same component is used for dialling and dispensing.

Figure 2:
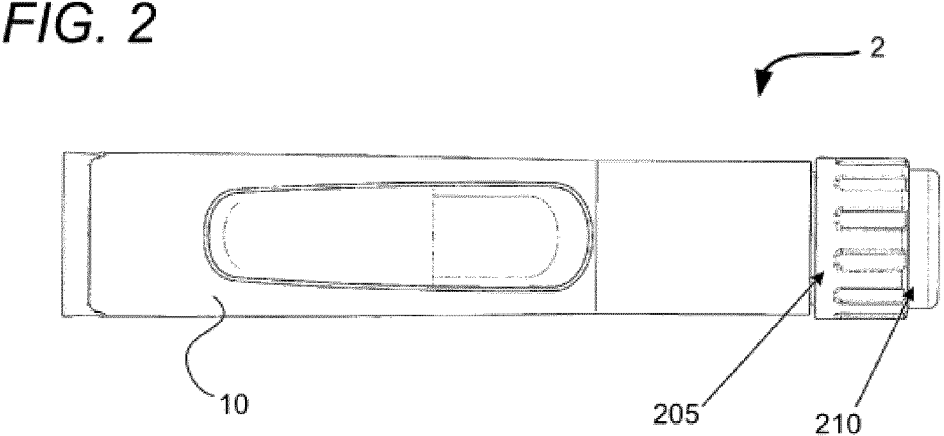
FIG. 2 shows a proximal end of an injection device according to a second embodiment.
Figure 3A:
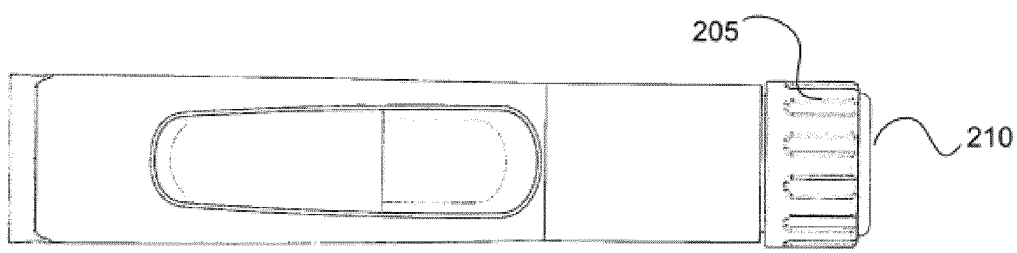
FIG. 3A shows a proximal end of the injection device of FIG. 2 after actuation of an injection button.
Figure 3B:
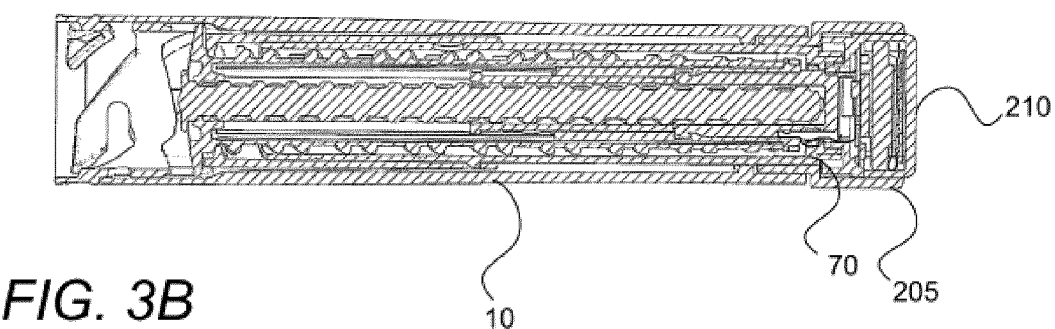
FIG. 3B is a cross-sectional view of the injection device of FIG. 2 after actuation of the injection button.

FIGS. 2, 3A and 3B show the proximal end of a device 2 according to a second embodiment. The device 2 comprises a grip 205 and injection button 210. Unlike the device 1 shown in FIG. 1, the injection button 210 is separate from the grip 205 which is used to dial the dosage. The dial sleeve 70 and injection button 210 are located partially inside the grip 205. The grip 205 and dial sleeve 70 may be considered functionally as elements of the same component. Indeed, the grip 205 and dial sleeve 70 may only be separate components for assembly reasons. Aside from the differences described herein, the device 2 shown in FIG. 2 operates in substantially the same way as the device 1 shown in FIG. 1.

Similarly to the device 1, the dial sleeve 70, grip 205 and injection button 210 extend helically from the device 2. During a dose-dialling mode of operation (as shown in FIG. 2) there is no relative rotation between the injection button 210 and the dial sleeve 70. The dose is dialed by rotating the grip 205 (thereby also rotating the dial sleeve 70 and injection button 210) with respect to the rest of the device 2.

To initiate dispensing of a medicament, the injection button 210 is pressed axially, as shown in FIGS. 3A and 3B. This action changes the mode of the device 2 to a dispensing mode. In dispensing mode the dial sleeve 70 and grip component 205 retract along a helical path into the rest of the device 2, whereas the injection button 210 does not rotate and only retracts with axial motion. Thereby, in dispensing mode, there is a disengagement of the injection button 210 leading to relative rotation of the injection button 210 with respect to the dial sleeve 70. This disengagement of the injection button 210 with respect to the dial sleeve 70 is caused by a clutch arrangement described in more detail in relation to FIGS. 8A-C.

Figure 4:
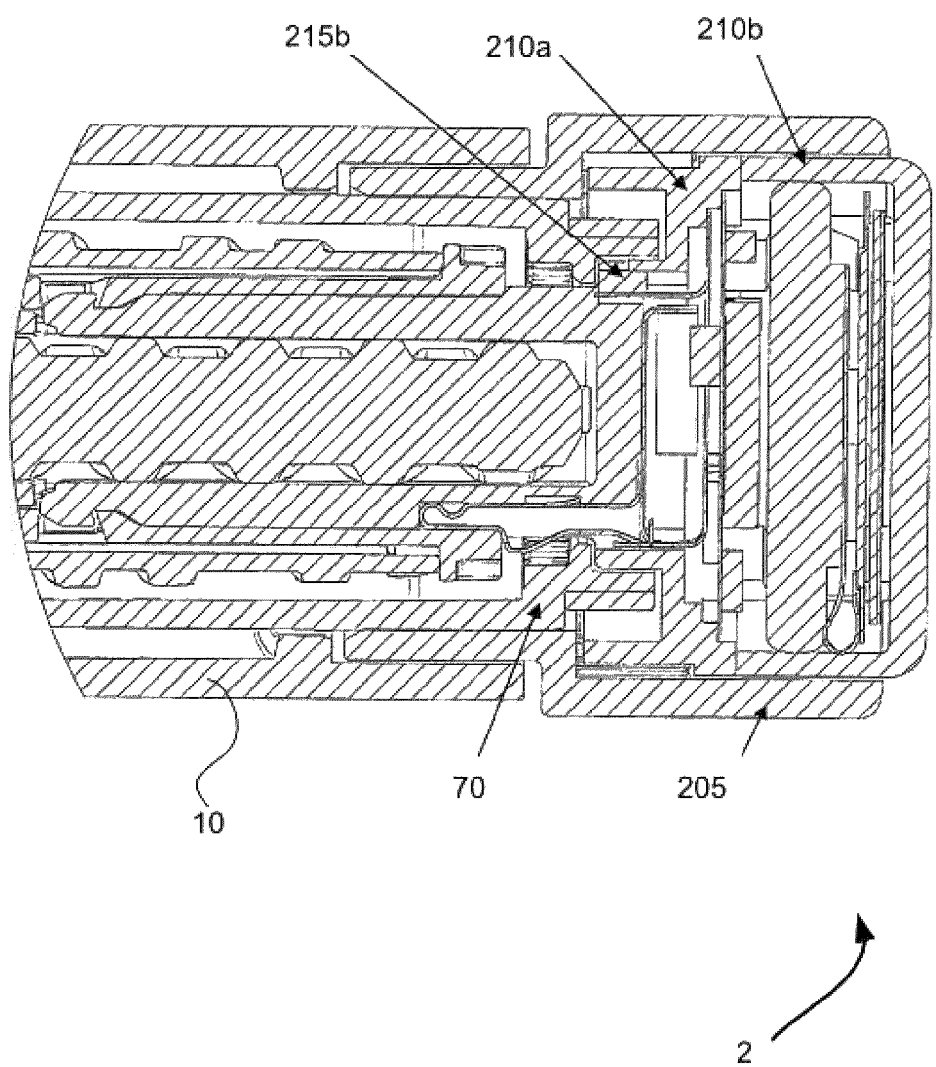
FIG. 4 is a zoomed-in cross-sectional view of the injection device of FIG. 2.

FIG. 4 is a close-up cross sectional view of the proximal end of the device 2 shown in FIG. 3 after the injection button 210 has been pressed. As shown in FIG. 4, the injection button 210 is configured as two separate sub-components, namely a distal or lower button part 210a and a proximal or upper button part 210b. The injection button 210 may be configured in this way to aid the assembly process. The distal button part 210a and proximal button part 210b may be fixed together and act functionally as a single component, i.e. the injection button 210.

A sensor arrangement 215 comprising one or more optical sensors is mounted in the injection button 210 which is configured to sense the relative rotational position of the dial sleeve 70 relative to the injection button 210. This relative rotation can be equated to the size of the dose dispensed and used for the purpose of generating and storing or displaying dose history information. The sensor arrangement 215 may comprise a primary (optical) sensor 215a and a secondary (optical) sensor 215b. In FIG. 4, only the secondary sensor 215b is shown.

Figure 5:
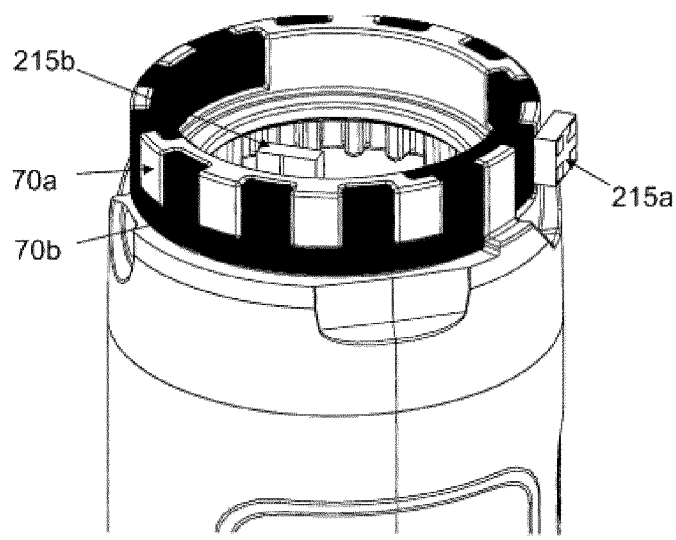
FIG. 5 is an elevated side view of a first type of encoder system.
Figure 6:
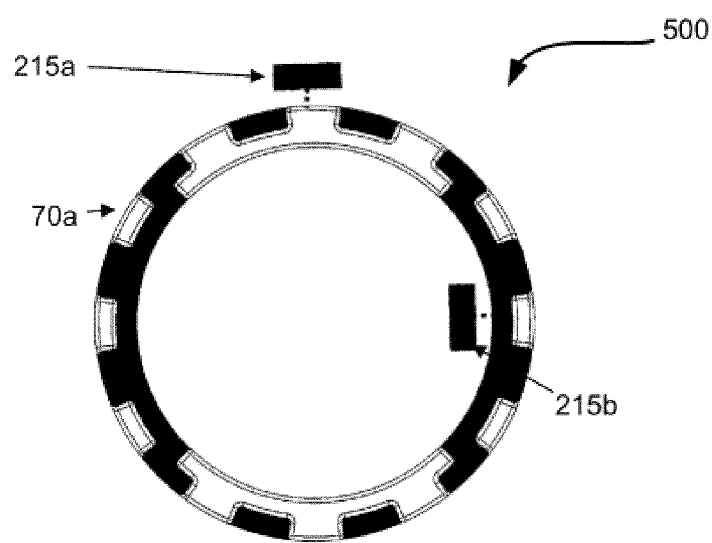
FIG. 6 is a plan view of the encoder system shown in FIG. 5.

FIGS. 5 and 6 show an encoder system 500 according to certain embodiments. The encoder system is configured for use with the device 2 described above. As shown in FIG. 5 and FIG. 6, the primary sensor 215a and secondary sensor 215b are configured to target specially adapted regions at the proximal end of the dial sleeve 70. In this embodiment, the primary sensor 215a and secondary sensor 215b are infrared (IR) reflective sensors. Therefore, the specially adapted proximal regions of the dial sleeve 70 are divided into a reflective area 70a and a non-reflective (or absorbent) area 70b. The part of the dial sleeve 70 comprising the reflective area 70a and a non-reflective (or absorbent) area 70b may be termed an encoder ring.

To keep production costs to a minimum, it may be favourable to form these areas 70a, 70b from injection moulded polymer. In the case of polymer materials, the absorbency and reflectivity could be controlled with additives, for example carbon black for absorbency and titanium oxide for reflectivity. Alternative implementations are possible whereby the absorbent regions are moulded polymer material and the reflective regions are made from metal (either an additional metal component, or selective metallisation of segments of the polymer dial sleeve 70).

Having two sensors facilitates a power management technique described below. The primary sensor 215a is arranged to target a series of alternating reflective regions 70a and non-reflective regions 70b at a frequency commensurate with the resolution required for the dose history requirements applicable to a particular drug or dosing regimen, for example, 1 IU. The secondary sensor 215b is arranged to target a series of alternating reflective regions 70a and non-reflective regions 70b at a reduced frequency compared to the primary sensor 215a. It should be understood that the encoder system 500 could function with only a primary sensor 215a to measure the dispensed dose. The secondary sensor 215b facilitates the power management technique described below.

The two sets of encoded regions 70a, 70b are shown in FIGS. 5 and 6 concentrically with one external and the other internal. However, any suitable arrangement of the two encoded regions 70a, 70b is possible. Whilst the regions 70a, 70b are shown as castellated regions, it should be borne in mind that other shapes and configurations are possible.

Figure 7:
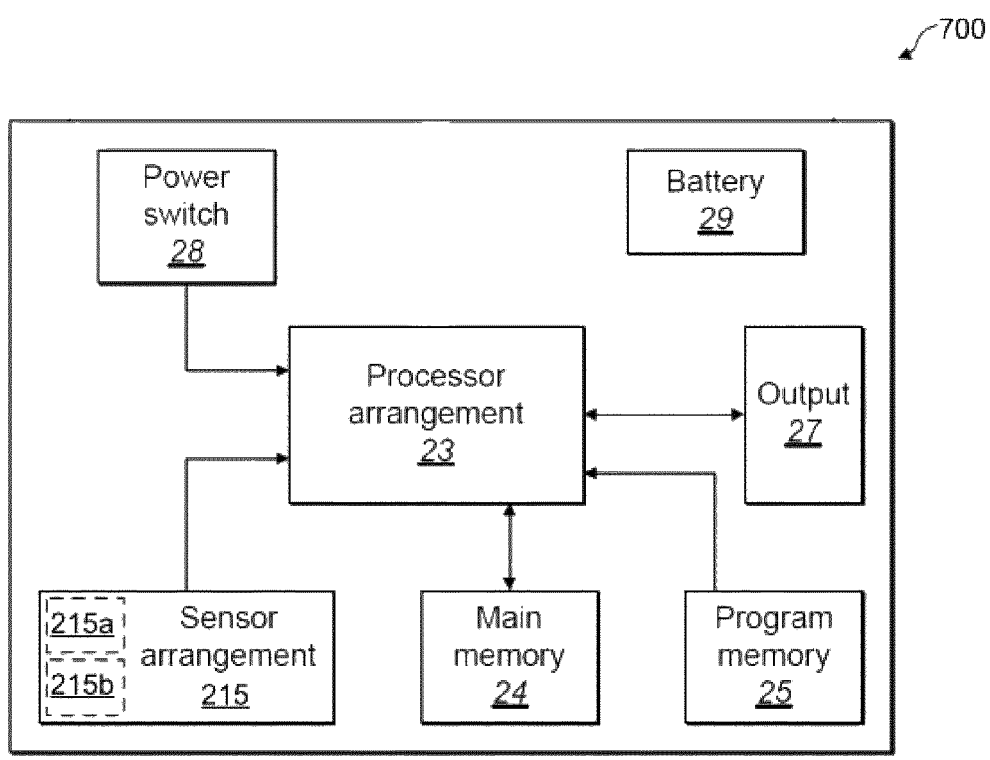
FIG. 7 is a schematic block diagram of a device controller.

The devices 1, 2 also include a controller 700, as shown schematically in FIG. 7. The controller 700 comprises a processor arrangement 23 including one or more processors, such as a microprocessor, a Digital Signal Processor (DSP), Application Specific Integrated Circuit (ASIC), Field Programmable Gate Array (FPGA) or the like, together with memory units 24, 25, including program memory 24 and main memory 25, which can store software for execution by the processor arrangement 23.

The controller 700 controls a sensor arrangement 215, comprising one or more sensors 215a, 215b, is provided.

An output 27 is provided, which may be a wireless communications interface for communicating with another device via a wireless network such as Wi-Fi or Bluetooth®, or an interface for a wired communications link, such as a socket for receiving a Universal Series Bus (USB), mini-USB or micro-USB connector. For example, data may be output to a data collection device attached to the device 1, 2.

A power switch 28 is also provided, together with a battery 29.

Power Management

It is advantageous to be able to minimise the power usage of the encoder system 500 so that the size of a battery 29 needed to be packaged into the device 1, 2 can be minimised. The sensors 215a, 215b used in this embodiment require a certain amount of power to operate. This embodiment is arranged such that the sensors 215a, 215b can be switched on and off intermittently at a controlled frequency (i.e. in a strobe-sampling mode). There is inherently a limit to the maximum rotational speed that can be counted by a sampled encoder system before aliasing occurs. Aliasing is the phenomenon where the sampling rate is less than the rate at which sensed regions pass the sensor which means that a miscount could occur when a region change is missed. The secondary sensor 215b with a reduced frequency compared to the primary frequency 215a can tolerate a higher rotational speed before it too becomes aliased. Whilst the secondary sensor 215b is not able to resolve the dose dispensed to the same resolution as the primary sensor 215a, the output of the secondary sensor 215b remains reliable at higher speeds. Therefore both sensors 215a, 215b are used in combination to be able to accurately determine dose delivered up to a first threshold rotational (dispensing) speed. The sensors 215a, 215b can then be used to determine an approximate dose delivered up to a second (higher) threshold dosing speed. At speeds above the second threshold speed the sensors 215a, 215b will not be able to accurately or approximately determine the dose delivered, therefore the second threshold is set above a speed which is not physically possible in the injection device 1, 2.

The first speed threshold is determined by the sampling rate of primary sensor 215a and the frequency of encoder region transitions, which is fixed at the resolution required by the intended drug or dosing regimen (for example one transition per 1 IU). The second speed threshold is determined by the sampling rate of the secondary sensor 215b and the frequency of encoder region transitions. The first threshold is set such that the largest range of dispensing speeds can be covered by the system for accurate reporting of dose dispensed.

The example embodiment shown in FIG. 6 has primary sensor 215a targeting region transitions at 1 transition per 1 IU of dose delivered and the secondary sensor 215b targeting region transitions at 1 transition per 6 IU of dose delivered. Other options are possible which include 1 transition per 2 IU, 1 transition per 4 IU, 1 transition per 8 IU and 1 transition per IU units. These options are each possible because there are 24 separate regions 70a, 70b per revolution in the encoder system 500 shown in FIG. 6. In general, if the number of separate regions 70a, 70b per revolution were n units then there would be options at one region transition per m units where m was any integer factor of n greater than 1 and less than n.

The slower the sampling frequency of both sensors 215a, 215b, the lower the power consumption required and therefore the smaller the required size of the battery 29. It is therefore optimal to minimise, by design, the sampling frequency as far as is practical.

Trigger Switch Arrangement

In order to further limit the battery capacity requirement, it is advantageous to be able to have the device 2 in a low power state when the sensors 215a, 215b are not required to be energised. This is achieved with a switch activated by the displacement of the injection button 210.

Figure 8A:
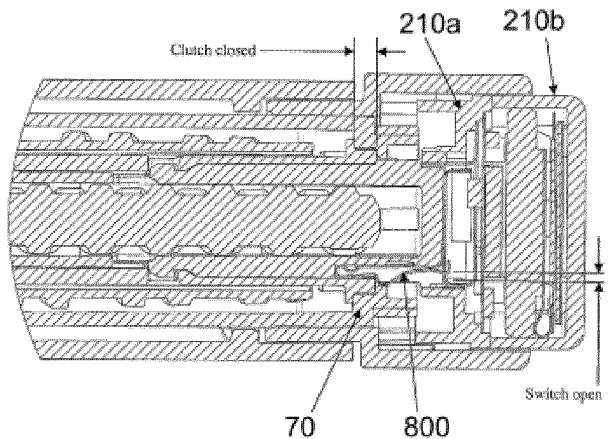
FIG. 8A is a cross-sectional view of the proximal end of a device before actuation of an injection button.
Figure 8B:
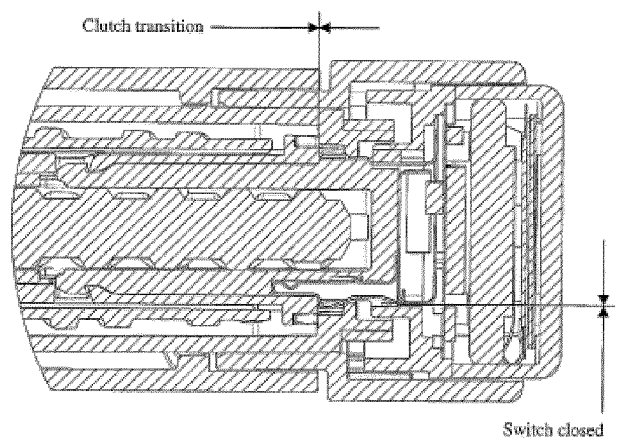
FIG. 8B is a cross-sectional view of the proximal end of a device during partial actuation of an injection button.
Figure 8C:
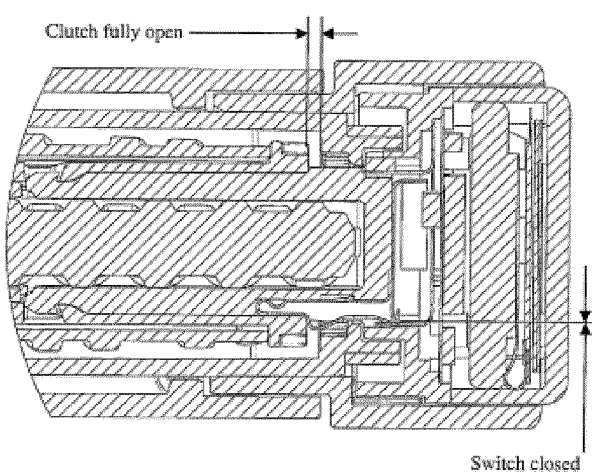
FIG. 8C is a cross-sectional view of the proximal end of a device during full actuation of an injection button.

As shown in FIG. 8A, a switch 800 is mounted in the injection button 210. In the configuration shown in FIG. 8A, an arm of the switch 800 is deflected by the dial sleeve 70 so that the switch 800 is in an open state. In this configuration a clutch between a clutch component and the dial sleeve 70 is engaged with the device 2 in its dialling mode. As the injection button 210 is pressed the injection button 210 is displaced axially with respect to the dial sleeve 70, therefore the switch 800 is displaced axially relative to the dial sleeve 70. This displacement causes a part on the dial sleeve 70 to ride down a cam surface on the switch 800, allowing the switch arm to deflect towards its free state. This deflection in the switch arm has the effect of changing the electrical state of the switch 800 (for example to electrically closed). The design is arranged such that the electrical change of state of the switch 800 happens before the state change in the clutch between the clutch component and dial sleeve 70. FIG. 8B shows the transition point of the clutch and shows that the switch 800 has already changed state. FIG. 8C shows the state of the device 2 with the injection button 210 fully pressed. In this condition, the clutch is fully separated allowing the clutch component and dial sleeve 70 to rotate relative to each other in the dispense mode.

This sequence operates in reverse when the injection button 210 is released.

The change in electrical state that occurs when the injection button 210 is pressed thereby allowing the device 2 to be powered down into a low energy consumption state when the injection button 210 is not pressed. Relative rotation between the injection button 210 and dial sleeve 70 is not possible, therefore the encoder system 500 is not required in this state.

It is possible for the mechanical configuration between the dial sleeve 70 and the switch 800 to operate in the opposite sense such that the arm of the switch 800 is deflected during dispensing rather than during dialling.

The following embodiments relate to an alternative sensing technique to determine the number of medicament units that have been dispensed from the device 1, 2.

As with the embodiments described above, two sensors 215 are mounted in the injection button 210 and are configured to sense the relative rotational position of the dial sleeve 70 relative to the injection button 210 during the dispensing of a dose. This relative rotation can be equated to the size of the dose dispensed and used for the purpose of generating and storing or displaying dose history information.

Figure 9:
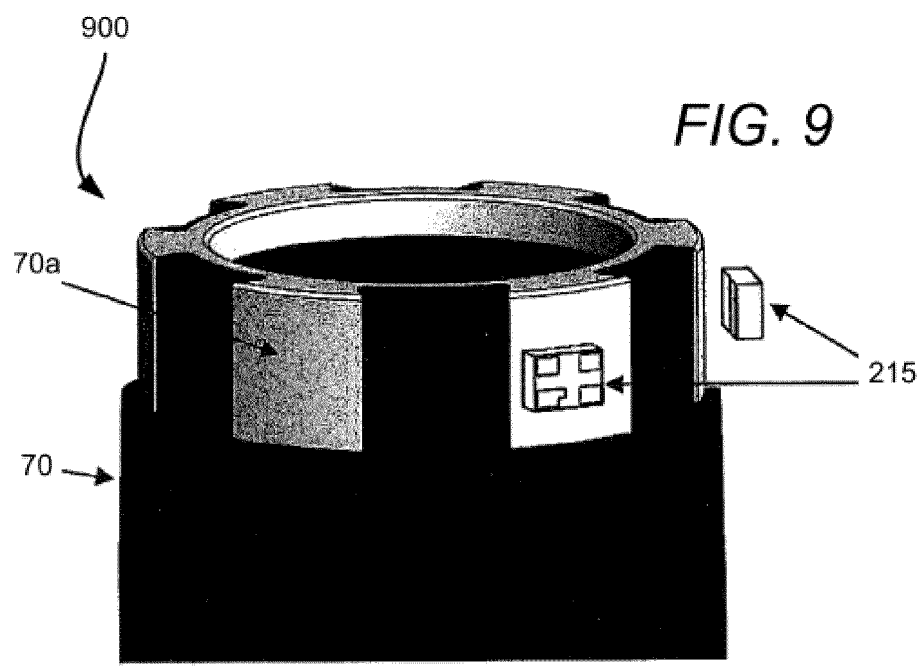
FIG. 9 is an elevated side view of a second type of encoder system.

As shown in FIG. 9, the two sensors 215 from this embodiment are configured to target specially adapted regions 70a, 70b of the dial sleeve 70. In this embodiment IR reflective sensors are used, therefore the regions of the dial sleeve 70 are divided into reflective and absorbent segments 70a, 70b. The segments 70a, 70b may also be referred to herein as flags.

Figure 10:
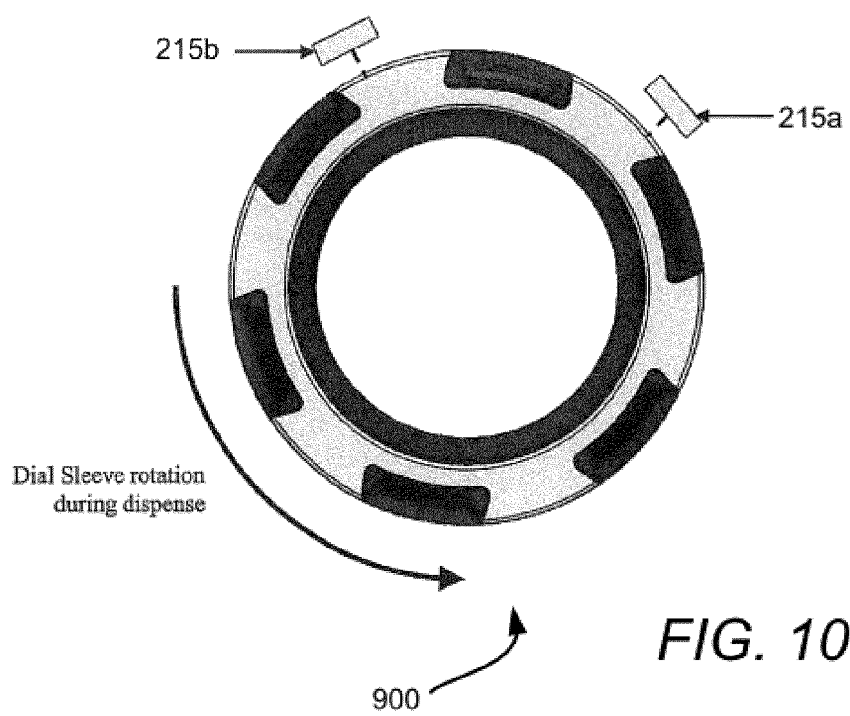
FIG. 10 is a plan view of the encoder system shown in FIG. 9.

Unlike the encoder system 500 described above in relation to FIGS. 5 and 6, the encoder system 900 shown in FIGS. 9 and 10 has both IR sensors 215 target the same type of region 70a, 70b. In other words, the sensors 215 are arranged so that they both face reflective regions 70a or both face absorbent regions 70b at the same time. During the dispensing of a dose, the dial sleeve 70 rotates anti-clockwise 15° relative to the injection button 210 for every medicament unit that has been dispensed. The alternate flag elements are in 30° (or two unit) sections. The sensors 215 are arranged to be out of phase with each other, such that the angle between them equates to an odd number of units (e.g. 15°, 45°, 75°, etc.), as shown in FIG. 10.

The encoder system 900 shown in FIG. 10 has 12 units per revolution, i.e. 12 alternating regions 70a, 70b. In general, embodiments work with any multiple of 4 units per revolution. The angle, α, between sensors 215 can be expressed by Equation 1, where both m and n are any integers and there are 4 m units dispensed per revolution.

$$\alpha = (2n-1)\frac{360}{4m} \quad \text{Equation 1-Angle between sensors}$$

Figure 11:
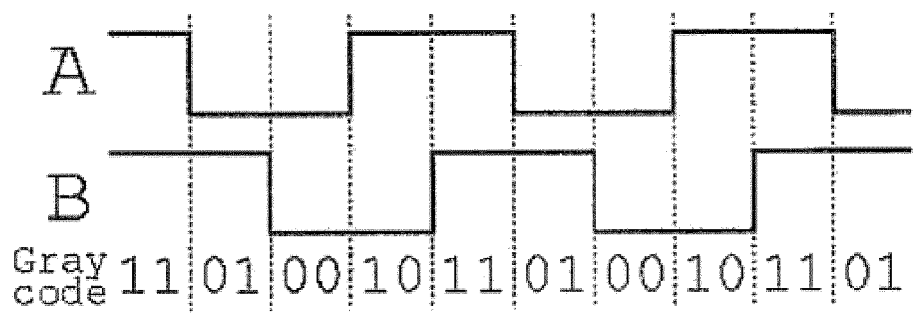
FIG. 11 illustrates a Gray code output.

FIG. 11 shows how the outputs for a Sensor A and Sensor B change as the dial sleeve 70 rotates anti-clockwise during dispensing of a medicament.

In combination, the two sensors A, B produce a 2-bit Gray code output (11, 01, 00, 10). The 2-bit code sequence repeats every four units dispensed. This coded output facilitates the detection of positive (anticlockwise) and negative (clockwise) rotations. For example, when the sensors read '11' a change to '01' would be a positive rotation and the change to '10' would be a negative rotation. This directionally sensitive system has advantages over a purely incremental system, in the ability to accurately determine true dispensed dose volume in the cases where negative rotations can occur. For example, in mechanisms that over rotate at the end of dose stop before 'backing-off' when the user releases the injection button 210.

Figure 12:
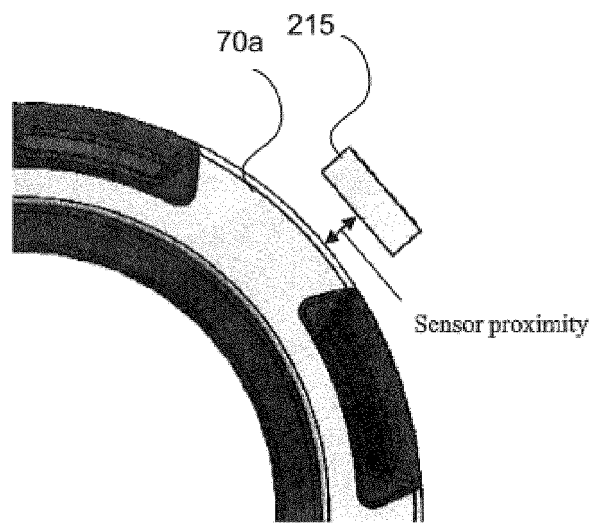
FIG. 12 is a partial plan view of an encoder system.

Referring to FIG. 12, the IR sensors 215 emit IR light from an LED. The IR reflective regions 70a of the encoder system 900 reflect the light and the sensors detect the reflected light. The sensors 215 then convert the detected light to an electrical output. The strength of the IR light that is detected by the sensor 215 after reflecting off the encoder ring is proportional to the proximity of the sensor to the encoder ring. Therefore it is desirable for the sensor 215 to be as radially close to the encoder ring as possible without contacting the encoder ring, which would add frictional losses to the dispense mechanism.

Figure 13:
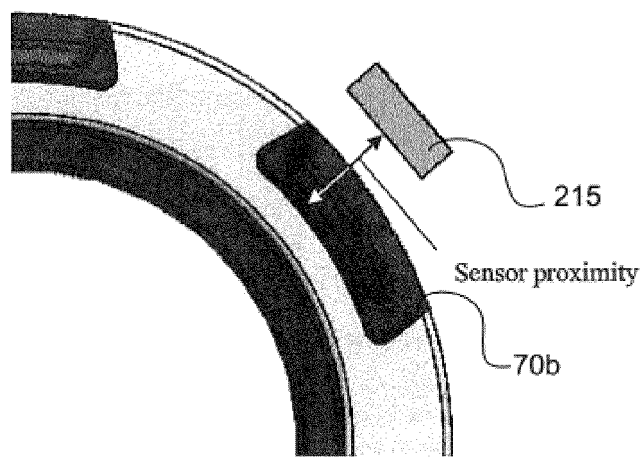
FIG. 13 is a partial plan view of an encoder system.

Referring to FIG. 13, the IR absorbent regions 70b of the dial sleeve 70 do not completely absorb all the IR light emitted from the sensor 215. Testing shows that when the sensor 215 is aligned with the absorbent regions 70b of the dial sleeve 70 the sensors 215 have some electrical output due to the low level of IR light reflected by the dial sleeve 70. Therefore, the dial sleeve flags have been designed to maximise the distance between the sensor 215 and any reflective parts of the encoder ring. This ensures a high contrast ratio and signal sharpness.

As a dose is dispensed, the software of the device 1, 2 monitors the electrical output of the sensors 215. The software detects changes between high and low outputs to determine when the relative rotation between the dial sleeve 70 and injection button 210 has reached an additional 15° (i.e. an additional one unit has been dispensed). Therefore it is beneficial to the function of the device for the contrast ratio between the high and low outputs to be as large as possible.

According to various embodiments, the design of the dial sleeve 70 and encoder ring flags 70a, 70b has been developed to increase the contrast ratio. The design shown in FIG. 14 has the absorbent dial sleeve flags 70b removed to leave gaps 140 between adjacent encoder ring flags 70a. This maximises the distance between the sensor 215 and any material which could reflect any of the IR light emitted from the sensor.

Figure 15A:
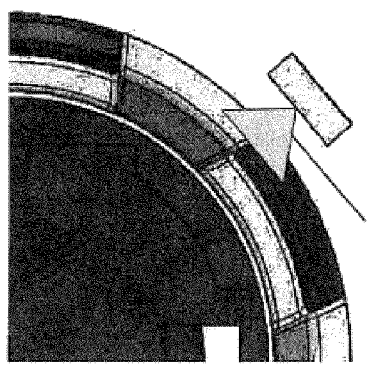
FIG. 15A is a partial plan view of an encoder system.

This design increases the contrast ratio between the low and high sensor electrical outputs. However, as FIG. 15A shows, the IR light emitted by the sensor 215 is not a beam, such that as the dial sleeve 70 rotates between a reflective encoder ring flag 70a and a gap 140, there is overlap where the sensor 215 detects some of the light emitted by the sensor 215. During this period, the sensor output gradually decreases from high to low, rather than an immediate step change between high and low. This gradual decrease is more difficult for the software to determine as a 15° rotation (i.e. one medicament unit dispensed), than an immediate step change.

Figure 14:
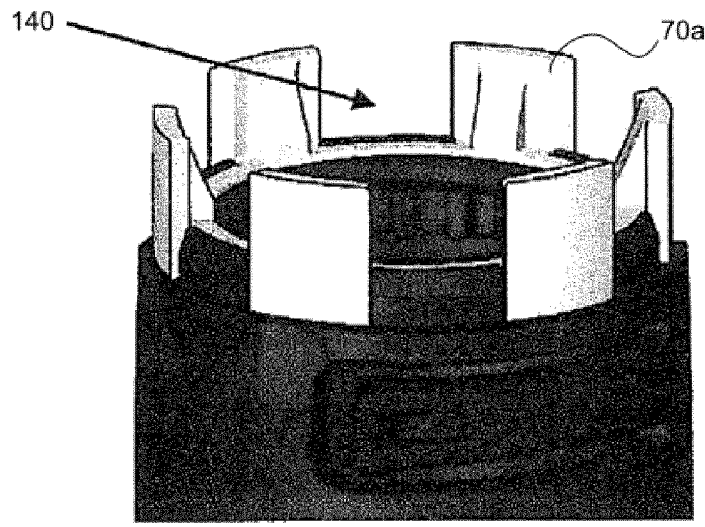
FIG. 14 is an elevated side view of a third type of encoder system.
Figure 15B:
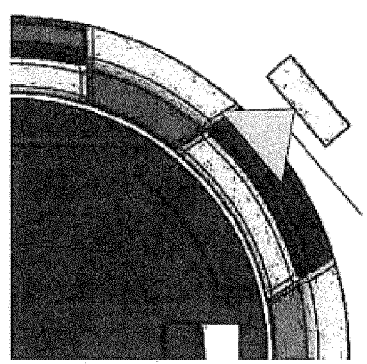
FIG. 15B is a partial plan view of an encoder system.

This phenomenon occurs with various embodiments of the encoder flags (as shown in FIG. 9 and FIG. 14). However, as shown in FIG. 15B, in accordance with certain embodiments, the rotation of the dial sleeve 70 that is required before the sensor output completely switches to a low output is increased due to the visibility of the sides of the reflective encoder ring flags 70a.

Figure 16:
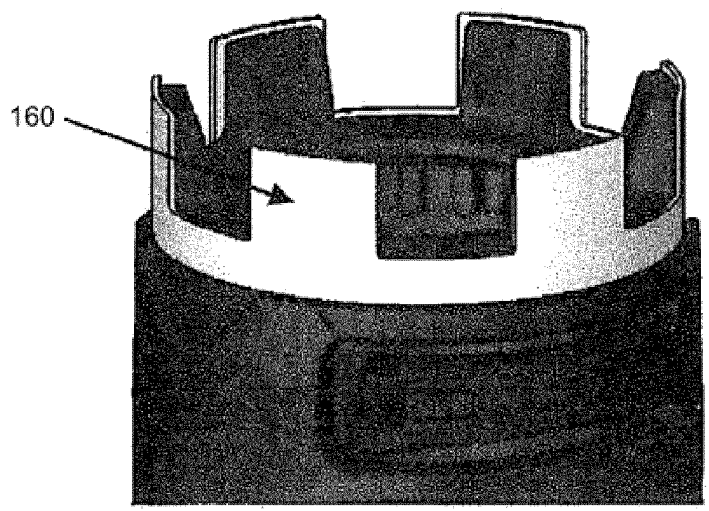
FIG. 16 is an elevated side view of a fourth type of encoder system.
Figure 17:
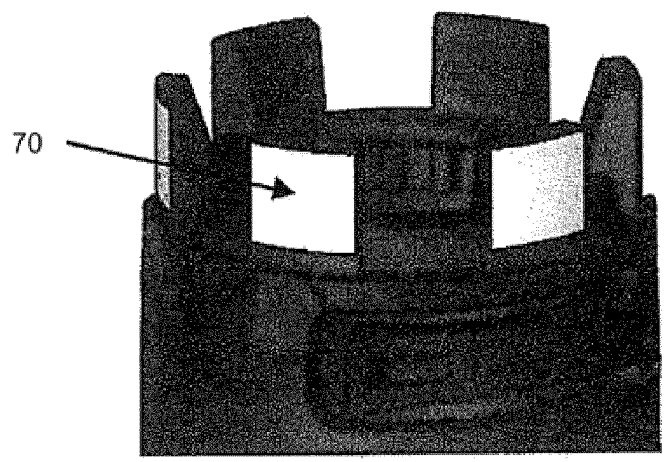
FIG. 17 is an elevated side view of a fifth type of encoder system.

Therefore, it is advantageous to reduce the thickness at the edges of the IR reflective flags 70a on the encoder ring. FIGS. 16 and FIG. 17 show two possible embodiments to reduce the thickness at the lateral edges of the IR reflective flags 70a on the encoder ring so that the reflective surfaces are inclined inwardly for preventing or reducing scattered reflection, thereby enhancing contrast transition and signal sharpness.

FIG. 16 shows an embodiment where the moulded polymer encoder ring has been replaced with a formed metal ring 160.

FIG. 17 shows an embodiment where the moulded polymer encoder ring has been replaced by sections of the dial sleeve 70 that have been printed, painted or coated with IR reflective material.

Figure 18A:
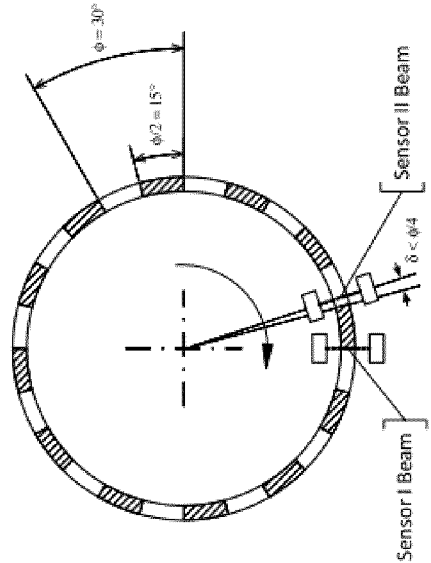
FIG. 18A is a plan view of a sixth type of encoder system.
Figure 18A:
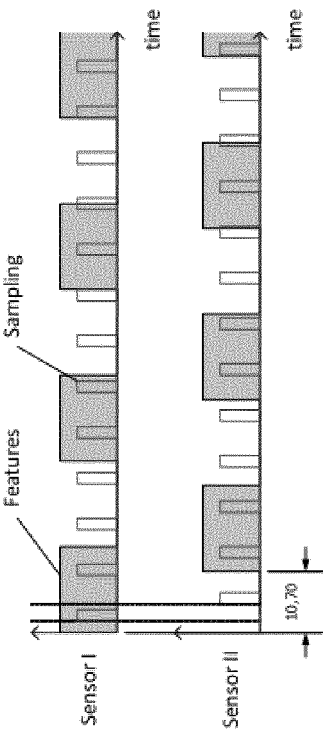
Figure 18B:
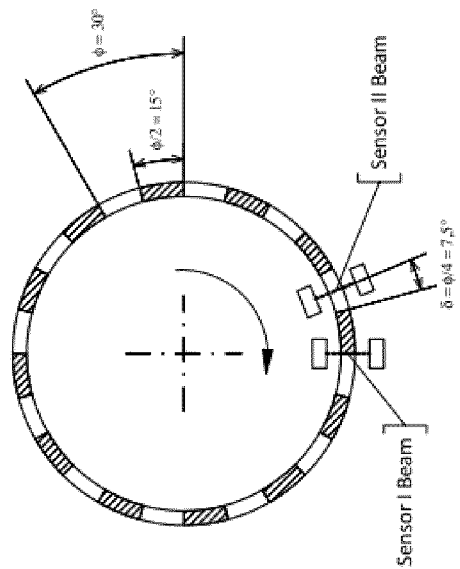
FIG. 18B is a plan view of a seventh type of encoder system.
Figure 18B:
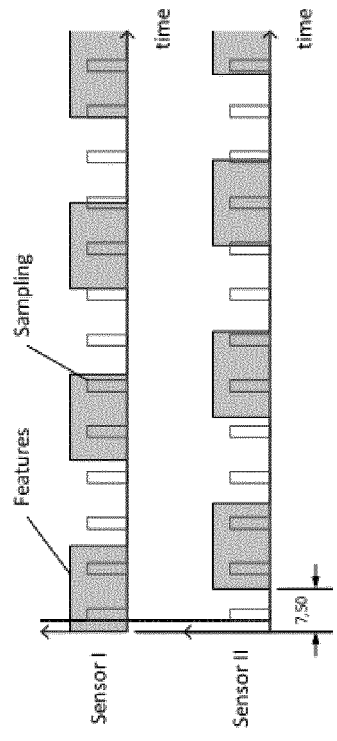

FIGS. 18A and 18B illustrate two alternative modes of operation in accordance with various embodiments. Referring to FIG. 18A, Sensor I and Sensor II are provided having an angular offset ($\delta$) is half of the periodicity ($\phi$) of the encoded regions of the encoder ring. In this embodiment, the sensors are operated to sample synchronously, i.e. at the same times ($t_1$, $t_2$, $t_3$, . . . ).

FIG. 18A illustrates an embodiment where the angular offset ($\delta$) differs from half of the feature periodicity ($\phi/2$) and the sensors are operated in a staggered mode with an offset in time ($\Delta t$) between samplings. This may be used to achieve more balanced overall system LED power consumption than available in synchronous operation.

In the configuration shown in FIG. 18B, the amount of the angular offset ($\delta$) may be decreased below half of the feature periodicity ($\phi$) in order to compensate for the relative angular travel during the offset in time ($\Delta t$) between the sampling operations of the different sensors.

The offset in time ($\Delta t$) may be adjusted according to an estimated value for the relative rotational speed ($\omega$) of the encoder ring which may be calculated from the sensor measurements. In particular, the offset time ($\Delta t$) may be decreased when an increase in rotational speed ($\omega$) is determined.

FIG. 19A shows scope traces obtained by embodiments of the disclosure. The lower trace is the LED driving signal and the upper trace is the output from the current mirror before the Schmitt trigger.

FIG. 19B is a zoomed-in view of the scope traces shown in FIG. 19A. Results show that it is possible to sample at 256 μs with a nearly 12-to-1 duty cycle (meaning the average current is $1/12^{th}$ of the 4 mA LED drive, thereby saving power and cell capacity. This is equivalent to a sample rate of over 3900 Hz and with one unit per segment and a minimum of two samples per segment a detection speed in excess of 1950 units per second is achieved without violating the Nyquist criterion. As such, no anti-aliasing detector is required.

FIG. 20 shows an embodiment of a method for varying the strobe of an LED of the sensors with the currently detected angular velocity. The highest trace in FIG. 20 represents the LED strobe, the lowest trace the acceleration of the sensors. The middle traces represent the signals generated by the sensors.

The strobe frequency of the LED may be kept at a low value as long as there is no change at the optical sensors and it can be assumed that the drive is at a standstill (angular velocity is zero).

With the first change of state at a sensor (the angular velocity is increased), the scanning frequency may be increased in order to detect the beginning rotation with sufficient accuracy. Furthermore, the frequency can be increased with increasing angular velocity in the manner of a tracking system, as shown in the lowest trace. In particular, this tracking can be set up in such a way that a loss in the resolution of the light barrier is sufficiently counteracted. Furthermore, the resolution at a detected angular velocity can particularly be set so high that even with the maximum acceleration of the drive to be considered, a sufficiently fast readjustment of the scanning frequency is possible.

Due to the acceleration, the signals of the sensors are not quite 90° symmetrical (as shown by the two middle traces in FIG. 20). As soon as the sensor rotates at a constant angular speed, the signals are exactly 90° offset.

In FIG. 20, it can be seen how with increasing angular velocity the illumination created by the LED strobe receives an ever higher scanning frequency in order to adjust the density, or duty factor, of the strobing along the time for always providing sufficient resolution in view of the actual motion state of the rotor.

Figure 20A:
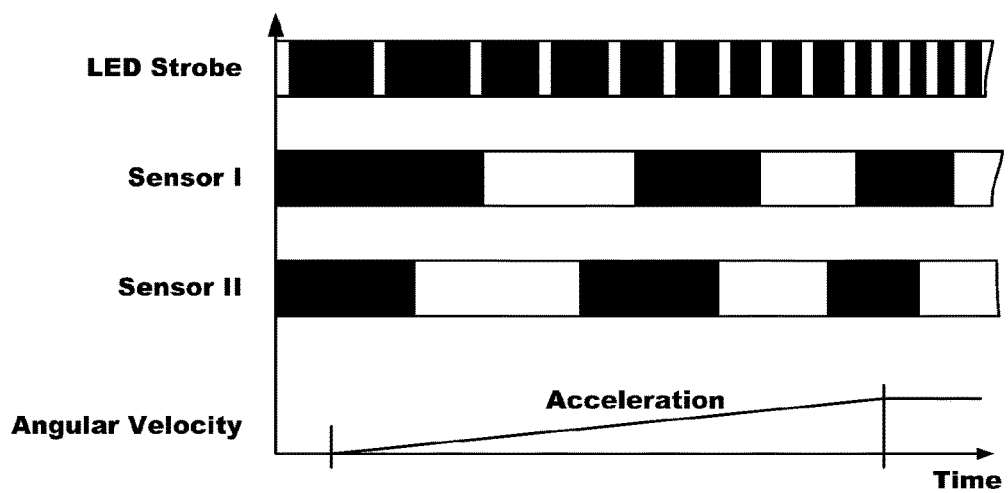
FIG. 20A shows a first method for varying the strobe of an LED of the sensors.

The four timelines provided in each of FIGS. 20A/B/C may help illustrating some exemplary embodiments for a method of an adaptive adjustment of the strobe frequency in accordance to the detected momentary angular velocity for achieving a trading-of between power saving and reliability in detection.

Here, for the sake of simplification it shall be assumed that the encoder illumination strobe is synchronous in the meaning of assuming both detectors being powered to produce light flashes of essentially the same length at essentially the same points in time. These strobe flashes are illustrated by the white gaps in the uppermost timeline denoted "LED Strobe". The black regions in between can be understood as the time intervals without any illumination on either sensor. Apparently, the mean power required for the sensor illumination corresponds to the number of strobes per time unit because of the constant strobe duration. In the exemplary situation of the exemplary strobe timeline in FIG. 20A, the increase in time density of the strobes from left to right therefore translates into a proportional increase in illumination power consumption. This increase, however, allows the sensors to correctly determine the operational state and velocity of the encoder rotor during phases of acceleration as will be explained subsequently.

In order to facilitate the understanding of the rotational kinematics of the mechanism coupled to the encoder rotor, the momentary angular velocity of the encoder rotor is provided in the lowermost timeline in each of FIGS. 20A/

B/C, denoted by "Angular Velocity". Again, for the sake of simplification in all three situations an acceleration model with piecewise linear behaviour has been chosen. In particular, it shall be assumed that the mechanism undergoes, after a short initial time at rest, a linear increase in angular speed, in the way of a constant acceleration and, after a more elongated time interval denoted "Acceleration", reaches a maximum rotational speed for the final time in consideration. This can be understood as a first order approximation to the dynamics of the mechanism under the assumption of a constant force being applied by the user for actuation. Due to the linear response of the conversion mechanism, a constant force will translate into a constant torque that can serve for acting against frictional effects in the baseline and for accelerating the mechanism. Additionally, as another simplification, it is assumed that the rotational speed will not increase beyond a maximum value whereat the overall frictional loss equals to the input torque. This is to reflect the fluid friction characteristic of the liquid expelling which, in a first approximation, monotonically increases with the flow rate of expelling. In the simplified model, the equilibrium is approached on a linear ramp as shown in the lowermost graph even though a more realistic modelling might rely on an asymptotic approaching to the maximum rotational speed. This, however, would not introduce a qualitative difference in view of the adaptive strobe sensor operation which shall be explained here.

Even though strobing based sensor operation has may yield some advantages in view of power consumption it suffers some systematic limitation when it comes to higher rotational speed or higher angular velocity. This can be understood more easily when looking at the second and third timelines where the continuous sensor intensity pattern in front of the respective optical sensor is illustrated. Here, "continuous intensity pattern" shall be understood as the intensity pattern the respective optical detector would detect under a fully continuous illumination without any gaps or interruptions over time. The effective detector reading, however, results from applying an "AND" operation to the value in the "LED Strobe" timeline and the respective "continuous intensity pattern" of the respective sensor. In a direct clue it can be derived, that in a situation wherein the strobes pulses match with either the darker or lighter areas in the "continuous intensity pattern" for a respective sensor in fixed phase relation, no change in the sensor reading will be observed and the signals might erroneously be interpreted by the processor towards a stationary angular position of the rotor. This may be considered as a worst case scenario wherein no valid information can be derived from the sensor signals at all in view of the rotational state. Apparently, there are other scenarios wherein only some information is lost in view of rotational transitions in one or another sensor. This can be imagined similar to a Moiré effect produced by the overlay of the strobe pulses and the moving brightness patterns.

Keeping this in mind, the timelines in FIGS. 20A/B/C may provide an example on how a generally more adequate scheme of increasing the strobe density along the time in response to a change in the rotational state of the rotor can help avoiding or at least reducing wrong sensor readings. A closer look to the "AND" between the first timeline and the second respective third timeline on the other hand indicates that a limited anticipatory increase in strobe density over time may already sufficiently address the issue when the mechanisms rotational acceleration can be assumed remaining below a known threshold value and/or when the maximum in angular velocity of the rotor can be assumed to remain below a known threshold value. As explained before these assumptions are fulfilled in a typical injection pen use case scenario wherein the accelerating torque is derived by mechanical conversion of the linear force a user applies to an actuation member, e.g. the dial extension.

Figure 20B:
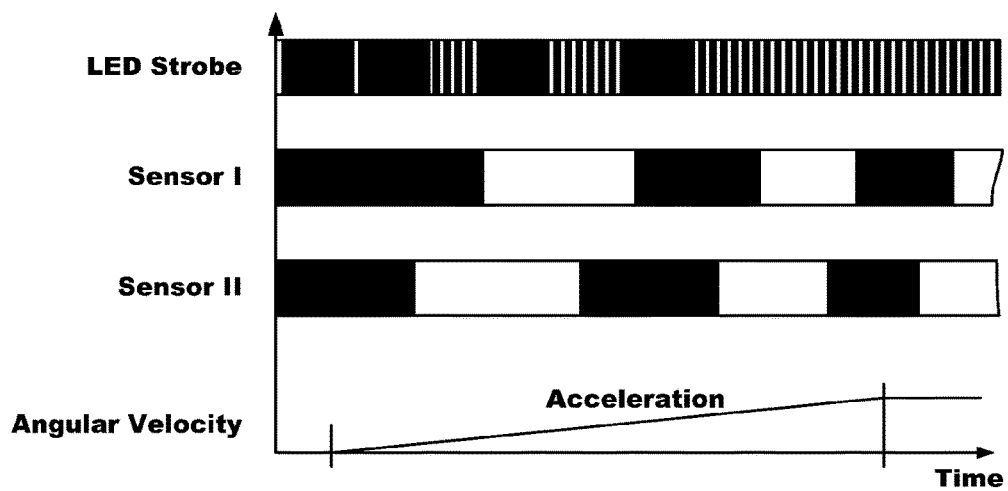
FIG. 20B shows a second method for varying the strobe of an LED of the sensors.

In view of this, a rather simple and easy to implement scheme for the adaption of the strobe density over time can be seen in a digital switching between a first, lower density value and a second, higher density value. Variants thereof are illustrated in FIGS. 20B/C. Both are designed for switching from the first value to the second value would be performed upon detection of the earliest transition from the stationary to the non-stationary situation and for switching back upon detection of a stationary state for a pre-determined amount of time. Clearly, the determination of whether a stationary state or a non-stationary state is reached has to be made on the basis of the sensor readings and some care has to be applied to avoid artefacts as explained before.

Figure 20C:
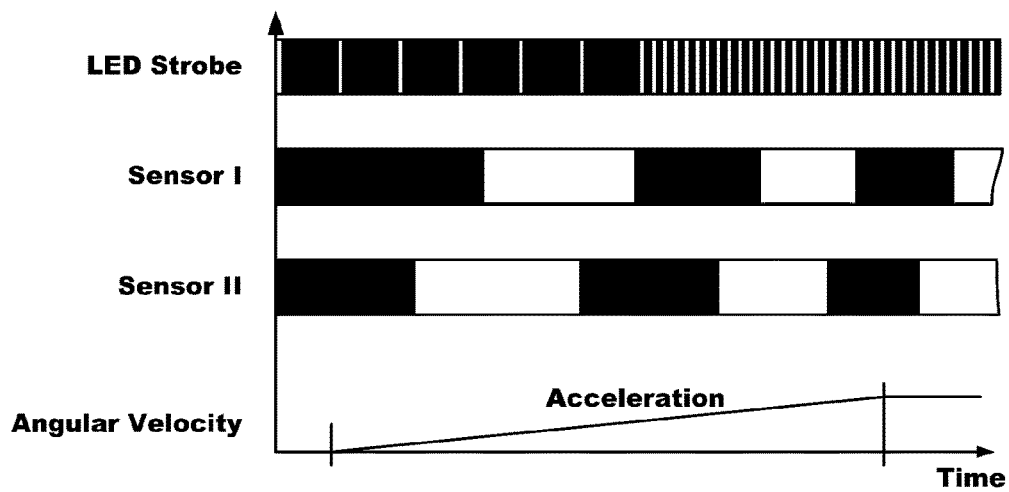
FIG. 20C shows a third method for varying the strobe of an LED of the sensors.

Specific variants on this general switching approach are illustrated in FIGS. 20B and 20C, respective. In particular, FIG. 20B provides an exemplary timeline for a "LED Strobe" density which is, directly after a transition in any of the sensors has been read, switched to the higher value and is maintained on this value until a pre-determined short time interval has lapsed without a further detection of a transition on the sensor readings. Apparently, this control scheme may result in toggling between the lower and higher value in phases of low angular speed of the rotor. FIG. 20C, in contrast, shows a "LED Strobe" that switches to the higher density value after the angular velocity value derived from the sensor readings exceeds a predetermined threshold value. This scheme would be completed by switching back to the lower value when the same threshold value or an even lower one is undershot by the calculated speed.

The appropriate selection of the specific values for the lower density and the higher density of the "LED Strobe" may find a starting point in the following considerations. Assuming the rotor to be in a stationary state, the first value has to be chosen to provide for sufficient density in order to capture the first transition in the "continuous intensity pattern" at either sensor and to allow switching of the strobe density to the higher value before the next transition passes in front of either sensor. Here, the critical value can be seen in the maximum in acceleration of the mechanism. Accommodation for higher acceleration requires more density in strobes at the stationary state and therefore needs an increase in the first, lower value. The critical condition for the second, higher value can be seen in the maximum speed. As explained before, the strobe density must be sufficiently not to produce any kind of artefacts. This very simple digital upwards/downwards switching may already provide significant increase in power efficiency for certain use cases wherein, after activation of the sensor operation, the delay in time before the mechanism transitions from a stationary state into a non-stationary state is not predictable and/or the time while the mechanism remains in the stationary state is significantly longer than the time while the mechanism is in the non-stationary state. Unpredictability, for example, may result from user behaviour. If, as a more specific example, the overall operation of the sensors is triggered in the way of a wake-up upon detection of a dose setting event or a cap removal event the delay in time until a subsequent expelling operation is started may depend on the time the respective user needs to place the needle and to start the expelling operation.

Other approaches for determining the increase or decrease in strobe density over time in order to accommodate for a change in the rotational state and/or velocity of the mechanism can be figured out on different levels of elaboration.

Additionally, in a situation with a staggered sampling mode wherein the strobing on the respective sensor has a shift in phase as, for example, explained with reference to FIG. 18B, an adaption of the shift in phase between the two sensors may be included. Insofar, the target might be seen in maintaining the phase shift in the "AND" reading as mentioned above between the angularly offset sensors on a constant value, e.g. 90°, independent of the momentary angular speed. The 90° situation would result in an overall detector behaviour identical to the one with exactly 90° offset sensors and synchronous sampling but apart of the need for powering all light sources at the same time.

Further variants to the outlined embodiment may include approaches for limiting the need of powering the LED strobing to only one of the two or more sensor. Apparently, at any point in the timeline of FIGS. 20A/B/C, from the two available sensor readings it can be determined whether the next transition will appear at either "Sensor I" or "Sensor II" because of the fixed spatial relationship of the sensors. In particular, for all points on the timeline with identical sensor readings, namely "dark"/"dark" and "bright"/"bright", the subsequent transition will appear in the timeline of "Sensor II". The same is correct for all points in time where "dark" would be read on the timeline of "Sensor I" while "bright" would be read on the timeline of "Sensor II". Only for time points where "bright" would be read from "Sensor I" whereas "dark" would be read from "Sensor II" the next transition can be predicted to appear in the timeline of "Sensor I". By applying this scheme, the power consumption for the strobe of the sensors could be further reduced at least in the stationary state of the mechanism.

An encoder system according to further embodiments will now be described with reference to FIGS. 21 to 29. This encoder system may be used to record doses that are delivered from the injection device. The concept of this encoder system is based on a light guidance used to convey the status of an indicator flag to a reflective sensor, which is located physically remote to the flag. The embodiments shown in FIGS. 20 to 28 are illustrated with an optical add-on module for an injection device, where the indicator flag is formed by a relative rotation of a number or the dial sleeve and the injection button, the latter of which houses an optical sensor. Such an add-on module may be configured to be added to a suitably configured pen injection device for the purpose of recording doses that are dialed and delivered from the device. This functionality may be of value to a wide variety of device users as a memory aid or to support detailed logging of dose history. The module may be configured to be connectable to a mobile device such as a smartphone or a tablet PC, or similar, to enable the dose history to be downloaded from the module on a periodic basis. However, the concept of the encoder system is also applicable to any device with the indicator flag and sensor separation, for example the injection device 1 of FIG. 1, wherein the module may be implemented in the dosage knob 12.

According to the encoder system concept, a collimating optics is arranged between the active face of at least one optical sensor, which may be a IR reflective sensor, and a movable dosage programming component. The collimating optics may comprise one or more discrete collimating lenses and one or more light pipes. The lens geometry may be selected to parallelize ("collimate") divergent radiation emitted by the at least one optical sensor prior to transmission through the light pipe between the at least one sensor and the target, namely the indicator flag.

Figure 21:
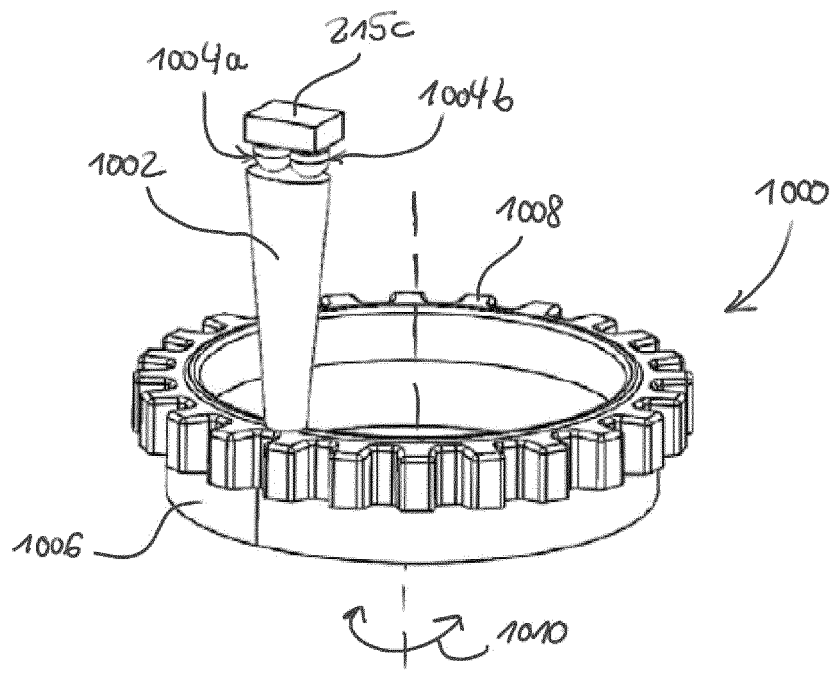
FIG. 21 is an elevated side view of an eight type of encoder system.

FIG. 21 shows essential parts of an embodiment of a module 1000 implementing this encoder concept: an indicator flag 1008 may be formed by relative rotation of a number sleeve 1006 around a rotation axis 1010, wherein the indicator flag 1008 is implemented in the shown embodiment by radially projecting teeth, formed in the top of for example the number sleeve or the dial sleeve 70 of the injection device 1; an optical sensor 215c and collimating optics comprising two collimating lenses 1004a, 1004b and a light guidance in the form of a light pipe 1002 for conveying the status of the indicator flag 1008 to the sensor 215c which is located remote from the flag. The collimating optics 1002, 1004a, 1004b and the optical sensor 215c may be positioned relative to surrounding components within the injection device and particularly associated to an add-on module. As can be seen, the collimating optics comprising the lenses 1004a, 1004 and the light pipe 1002 are arranged between the active side, i.e. the IR emitting and receiving side of the optical sensor 215c and the indicator flag 1008 formed by the number sleeve 1006.

Figure 22:
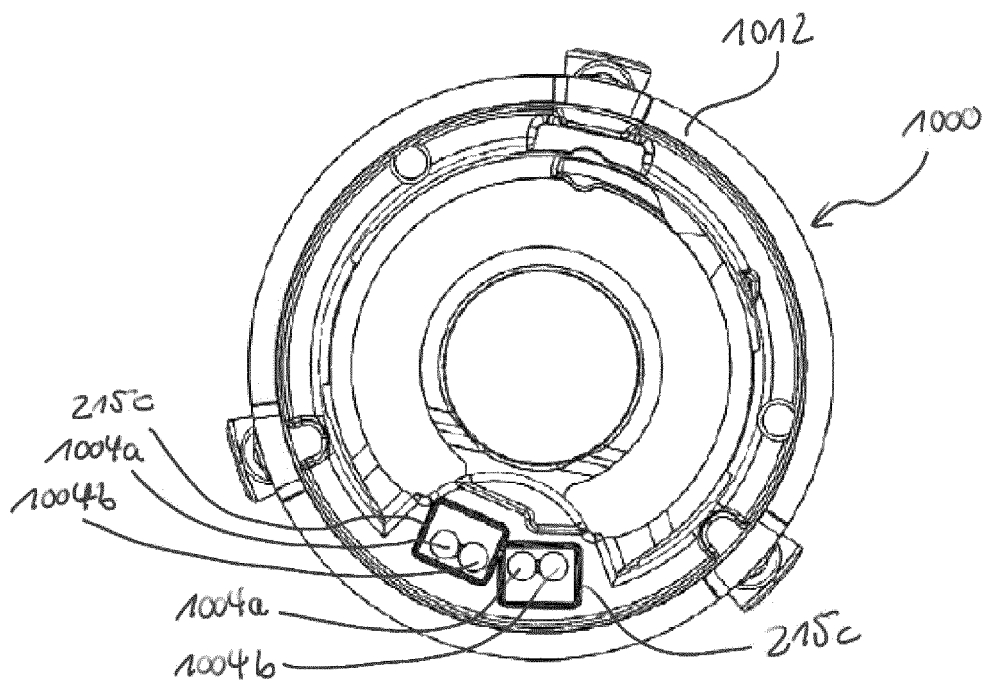
FIG. 22 is a plan view of the encoder system shown in FIG. 19.

FIG. 22 shows a chassis 1012 housing two optical sensors 215c (represented by their locations in the chassis 1012 shown by the rectangles with bold lines) and their respective collimating lenses 1004a, 1004b according to an embodiment of a module 1000. The collimating lenses 1004a, 1004b, here implemented by discrete lenses, are envisaged to be held relative to the optical sensors 2015c and proximal face of the light pipes by means of a cradle or other locating geometry existing as a feature within the chassis 1012.

Figure 23:
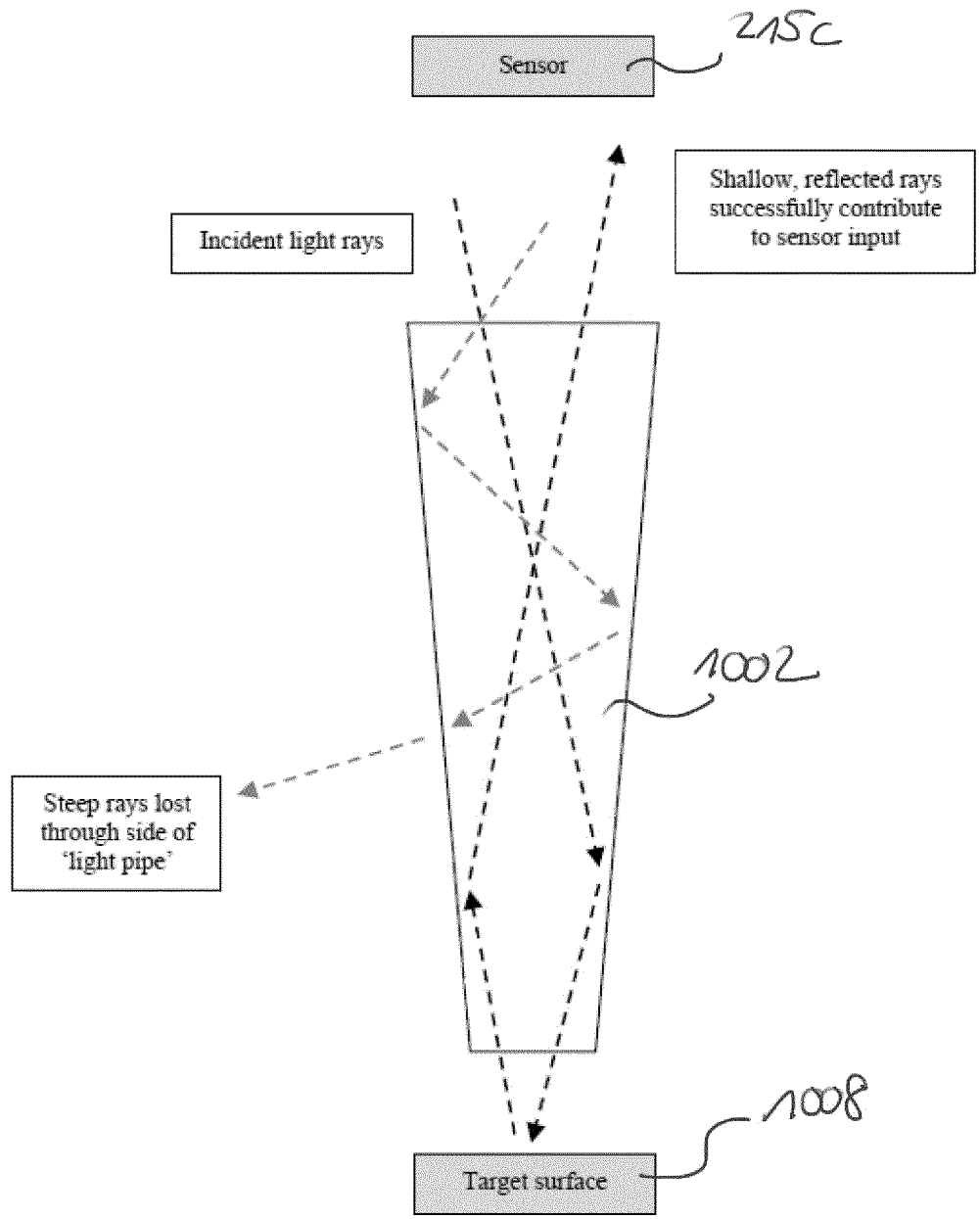
FIG. 23 is a schematic for demonstrating the light guidance with a light pipe of a sensor arrangement used in the eight type encoder system of FIGS. 20 and 21.

FIG. 23 shows the light pipe 1002 and the guidance of radiation (represented by the dotted arrows) within the light pipe 1002. The sensor 215c is arranged in front of the distal end of the light pipe 1002, and the target surface, i.e. the indicator flag 1008, in front of the pipe's proximal end. The diameter of the light pipe reduces from the distal to the proximal end so that the light pipe 1002 has the shape of a frustum. Particularly, the light pipe 1002 may have a circular or an elliptic cross section. The light pipe 1002 helps to better guide radiation emitted by the sensor 215c to the remote target face or indicator flag 1008, respectively, and radiation reflected from the indicator flag 1008 back to the receiving part of the sensor 215c. Thus, the signal received by the sensor viewing a reflective surface (the number sleeve) via the light pipe may be improved, which results in a better signal quality due to the improvement in response of the optical sensor as a result of a greater incident flux on the receiver of the optical sensor, which is particularly during normal operation as it may increase the voltage output of the optical sensor and a higher voltage output may be more easily detectable.

Figure 24:
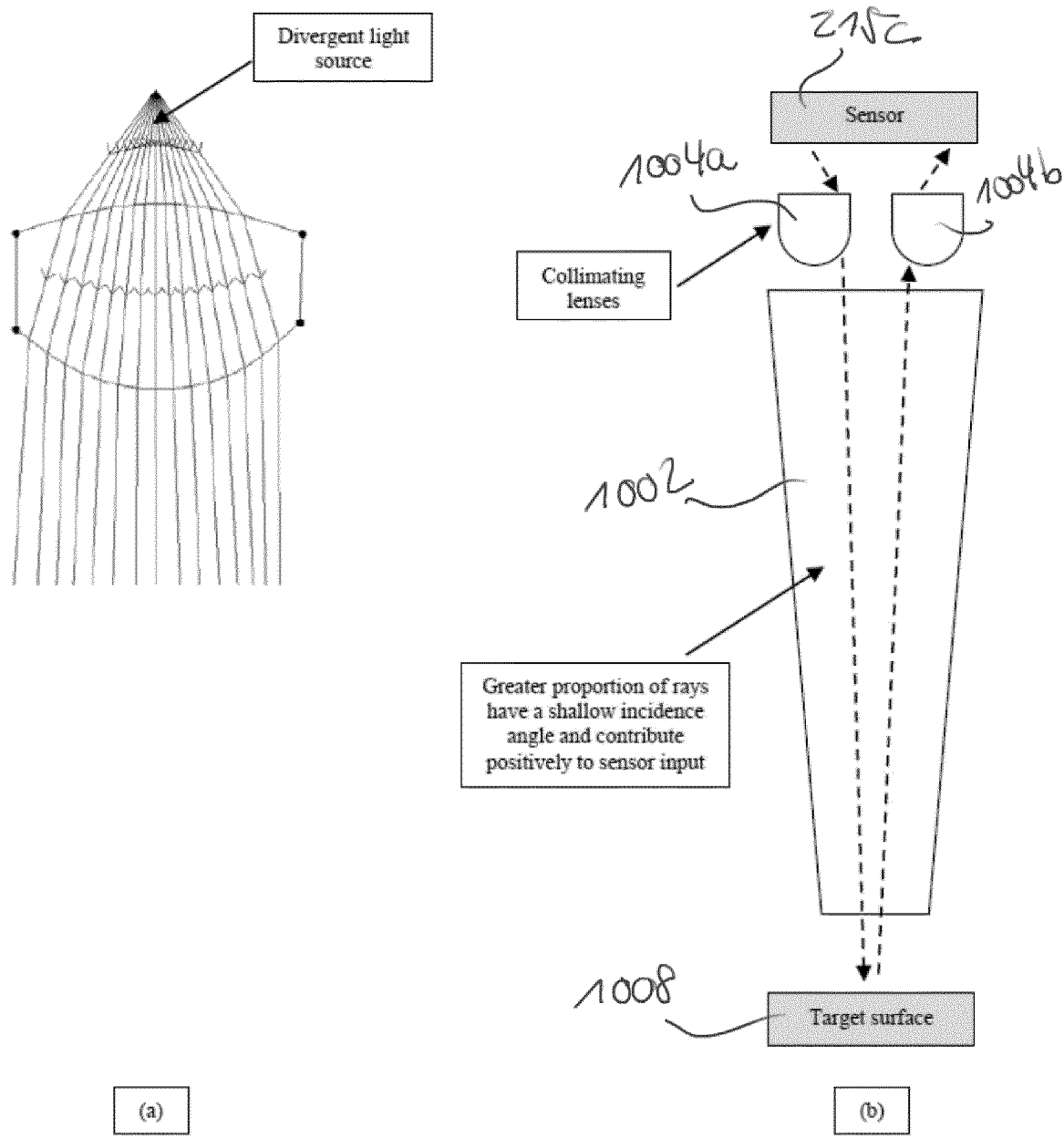
FIG. 24 is a schematic for demonstrating the light guidance with a light pipe and collimating lenses of a sensor arrangement used in the eight type encoder system of FIGS. 20 and 21.

FIG. 24 shows in picture (b) the effect of discrete collimating lenses 1004a and 1004b arranged between the distal end of the light pipe 1002 and the sensor 215c. Divergent radiation emitted by an active part of the sensor 215c is collimated with the collimating lens 1004a before transmission through the light pipe 1002 to the indicator flag 1008 representing the target surface. The radiation reflected by the indicator flag 1008 back into the light pipe 1002 is guided to the collimator lens 1004b which collimates the received radiation before it is received by the receiving part of the sensor 215c. The collimating lens 1004a particularly serves to collimate the radiation of a divergent light source such as in LED (Light Emitting Diode) of the sensor 215c, as shown in the left picture (a) of FIG. 24. It is envisaged that the collimating lenses 1004a, 1004b may be made of an optically transparent material, such as glass or polycarbonate, particularly with a good infrared transmissivity in the wavelength range of the optical sensor 215c. To minimize any impact to an increased length of the module comprising the collimating optics and the sensor, it is anticipated that the collimating lenses of the collimating optics should take the form of lenses featuring aspheric, or non-constant-curvature surfaces, which permit a collimating effect to be achieved in a smaller form factor optic, as exemplarily shown by the lens in picture (a) of FIG. 24. Particularly, the detection of a binary state of a number sleeve target during a "mode shift", i.e. when the dose or injection button of an injection device is being depressed from its relaxed state into its 0U position, can be improved with the collimating lenses. In this case, differentiation between a binary '0' and '1' as detected by the optical sensor can be readily obtained for a large, for example ~0.5 millimeters, separation between the distal ends of the light pipes and the number sleeve, with components undergoing relative rotation. Incorporation of the collimating lenses may reduce the divergent effect of the aforementioned gap, facilitating disambiguation between a '0' and a '1' as reported by the optical sensor. Another advantage of the use of the collimating lenses is the possible reduction of "cross-talk" (light leakage) between neighbored sensor where the outputs from such sensors are sharing the same optically contiguous light pipe chassis.

All of the above points relate, fundamentally, to more robust encoding mechanical system where an optical (reflective) sensor form the active element in an optical encoder. If the motion of the number sleeve relative to the dose button is more efficiently captured, reduced emitter power of an optical sensor and the use of algorithms requiring fewer microcontroller operations can be utilized, reducing energy consumption and extending battery life. The encoder system described above and in the following with reference to FIGS. 20 to 28 is equally applicable to inclusion in a disposable or a re-usable injection device, or any device containing an optical encoder arrangement with a similar light pipe architecture.

Figure 25:
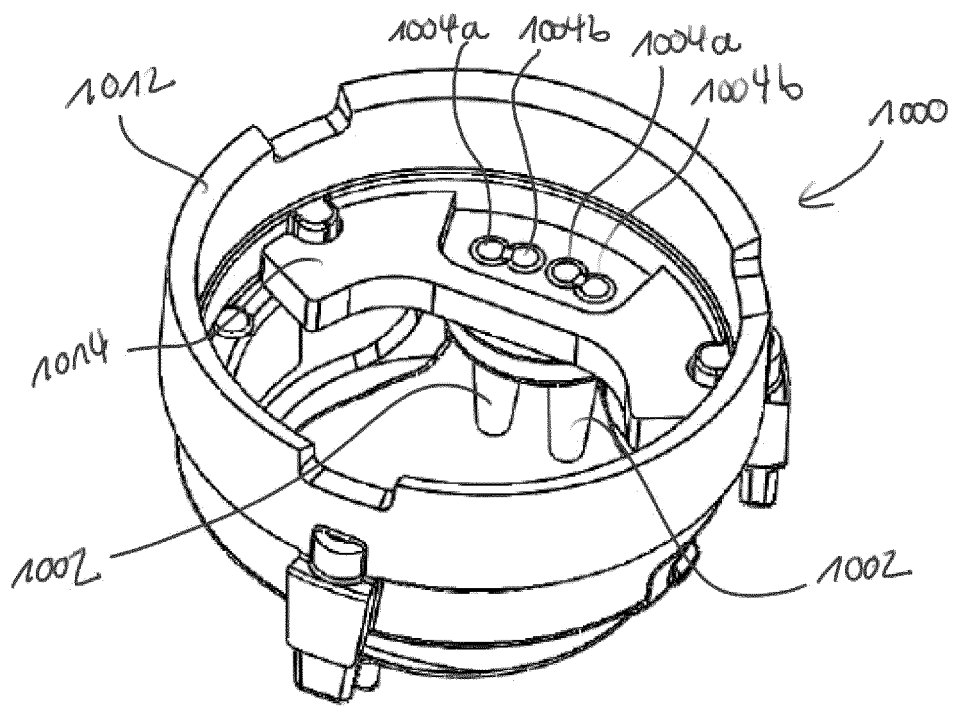
FIG. 25 is an elevated side view of an electronic module sub assembly comprising a separate injection moulded component with a light guidance.
Figure 26:
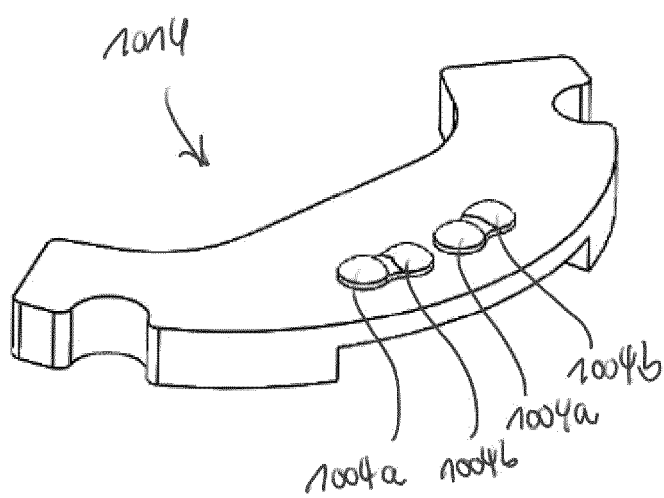
FIG. 26 is an elevated side view of the separate injection moulded component comprising collimating lenses of the light guidance.

The collimating optics may be implemented as individual, discreet components distinct from an injection moulded light pipe chassis. FIG. 25 shows a further embodiment of a chassis 1012 comprising a separate injection moulded component 1014 fixed in the chassis 1012, which is provided as holder for all elements of the collimating optics, namely the collimating lenses 1004a, 1004b, and the light pipes 1002. The component 1014 with the attached collimating lenses 1004a, 1004b and separated from the chassis 1012 is shown in FIG. 26.

Figure 27:
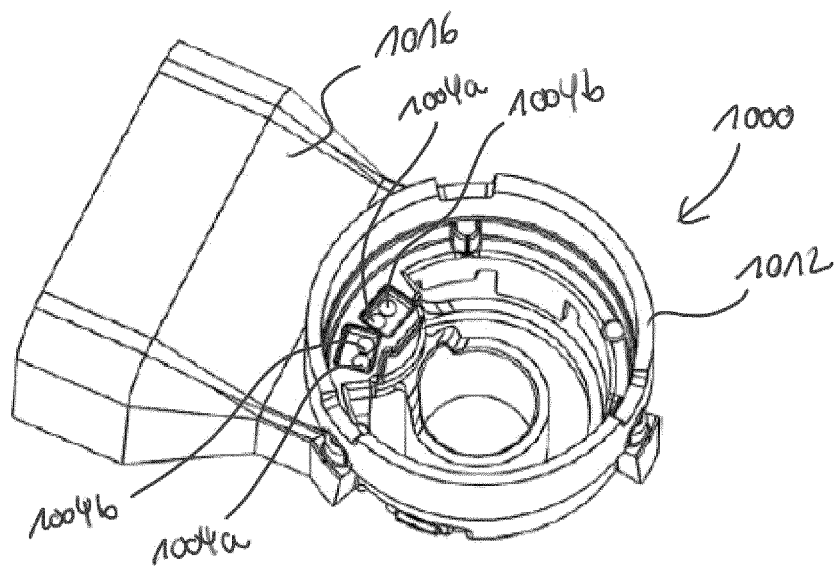
FIG. 27 is an elevated side view of another electronic module sub assembly comprising an integrally injection moulded collimating lenses assembly of a light guidance with a tool side-action to form distal surfaces of the collimating lenses.
Figure 28:
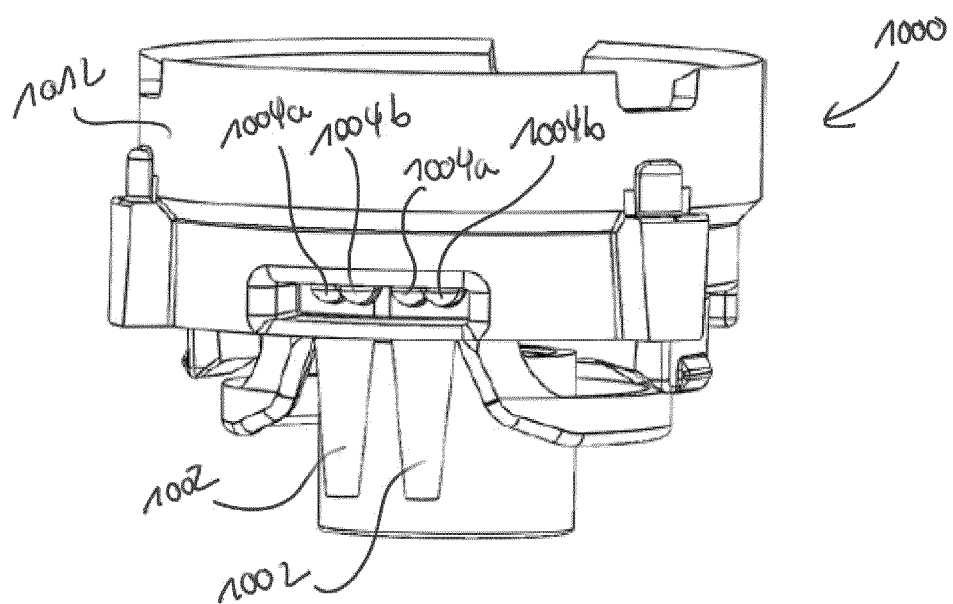
FIG. 28 is a side view of the electronic module sub assembly of FIG. 27 showing the formed distal surfaces of the collimating lenses.
Figure 29:
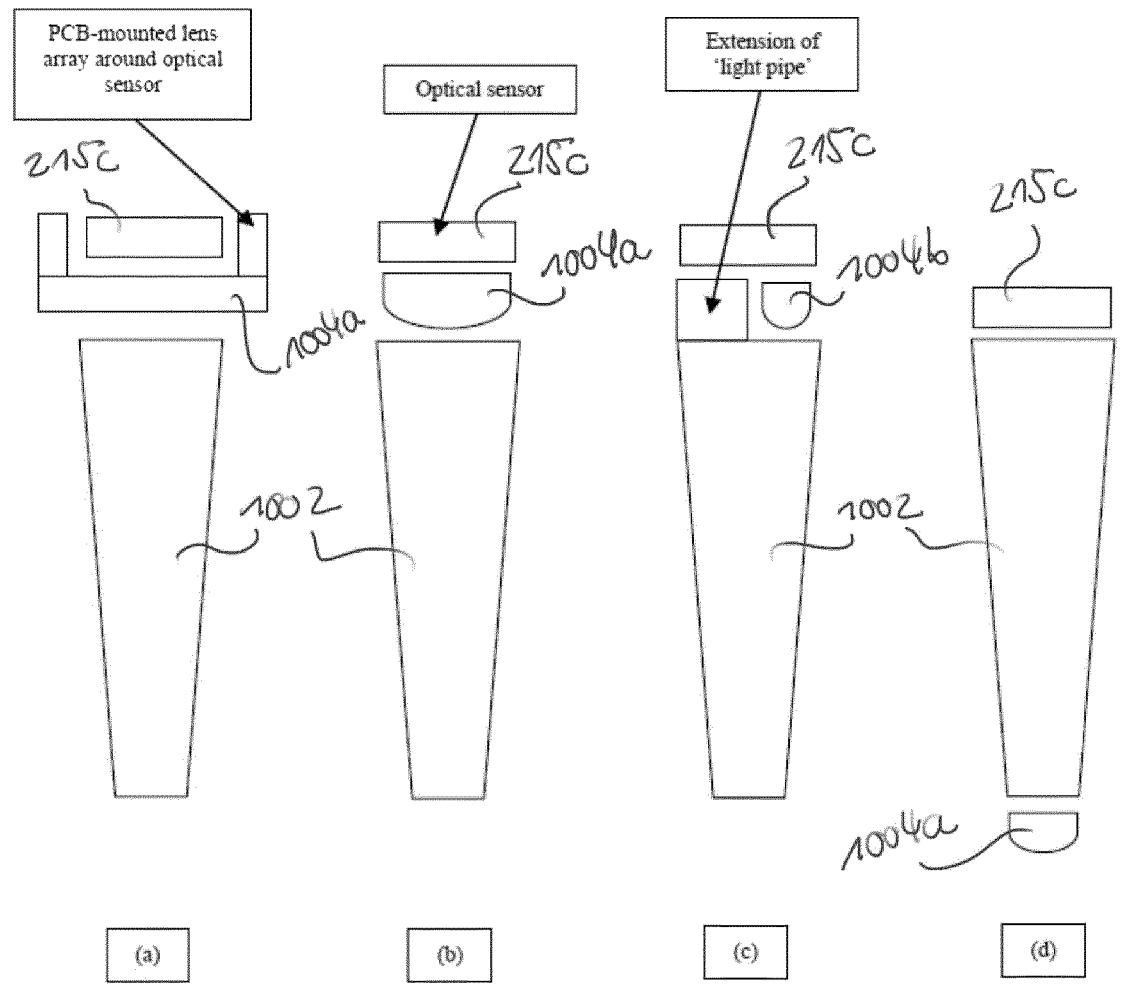
FIG. 29 shows four schematics of four alternative collimating lens assemblies for implementing a light guidance for the eight type of encoder system.

Alternatively, the collimating lenses geometry can also be formed directly by part of a tool 1016 provided for creating the light pipe chasses 1012, as shown with the embodiment of FIG. 27. In this case, the lower portion of the lens geometry may be limited to hemispheres owing to the tool action, while the proximal surfaces can be formed as full (a)spheres. FIG. 28 shows the integral injection moulded chassis 1012 comprising also light pipes 1002.

The embodiments described above use two discrete collimating lenses 1004a, 1004b covering, individually, the transmitting and the receiving portions of the optical sensor, particularly, the optical infrared reflective sensor. However, also other embodiments are possible, as will be described with reference to FIG. 29 in the following: for example, picture (a) shows an embodiment with a PCB (Printed Circuit Board) mounted, micro-moulded lens array 1004a covering the sensor 215c; another example is shown in picture (b), where a single collimating lens 1004a is provided, which covers both the transmitting and receiving portions of the optical sensor 215c; further embodiments with a single collimating lens are shown in pictures (c) and (d): the embodiment of picture (c) uses a single collimating lens 1004b covering the receiving portion of the optical sensor 215c, and the embodiment of picture (d) uses a single collimating lens 1004a placed at the distal end of the light pipe 1002.

Next, embodiments of algorithms for processing the signals, particularly signal voltages, generated by the optical sensors of sensor arrangements as described above with regard to the injection device and the module are described. The algorithms are implemented as computer programs for execution by one or more processors, for example of the processor arrangement 23 comprised by the controller 700 as shown in FIG. 7.

The algorithms are implemented for processing the signals delivered by the one or more optical sensors 215a, 215b, 215c, namely for decoding the selected for delivery by or delivered by an injection device. The algorithms are particularly applicable to the module described above with reference to FIGS. 20 to 28 but is also applicable to the injection device described above with reference to FIGS. 1 to 19B. The algorithms are preferably applicable to devices with an indicator flag and sensor separation with light pipes such as the module as described above. The relative rotation between the dose button and the number sleeve may be encoded optically using an incremental encoder, for example a quadrature encoder, with two or more optical sensors, particularly reflective IR sensors, looking axially at castellations or radially projecting teeth, formed on the top surface of the number sleeve. The encoder system may be implemented as an add-on module as described above with reference to FIGS. 20 to 28, which means that the position of the castellations or teeth being detected may vary relative to the positions of the optical sensors from device to device. Additionally, while the dose button is being depressed and released, the axial position of the optical sensors may also vary relative to the castellations.

The algorithms described in the following may be implemented in an injection device or an add-on module particularly for the purpose of recording doses that are delivered from the injection device. This functionality may be of value to a wide variety of injection device users as a memory aid or to support detailed logging of dose history. It is envisaged that the electronics implementing the algorithms may be configured to be connectable to a mobile device such as a smartphone, or similar, to enable the dose history to be downloaded from the electronics on a periodic basis.

The algorithms are configured for detecting the relative rotation of castellations or teeth on a number sleeve relative to a non-rotating component such as the dose button. The presence or otherwise of a castellation or tooth feature provides a binary code, which may be used to count the number of units dispensed from the injection device. The voltage output of the optical sensors may be typically approximated to a sinusoid. The algorithms are able to detect the presence or otherwise of a castellation or tooth feature across all devices, which may have any combination of geometrical tolerances on the physical features.

Additionally, as the dose button moves axially towards or away from the castellation or tooth features at the beginning and end of dose ejection, the change in the signal generated by the optical sensor should not be incorrectly interpreted as a rotation of the castellation or tooth features. Therefore, the algorithms may accommodate significant amplitude modulation of the signal generated by the optical sensor.

Figure 30:
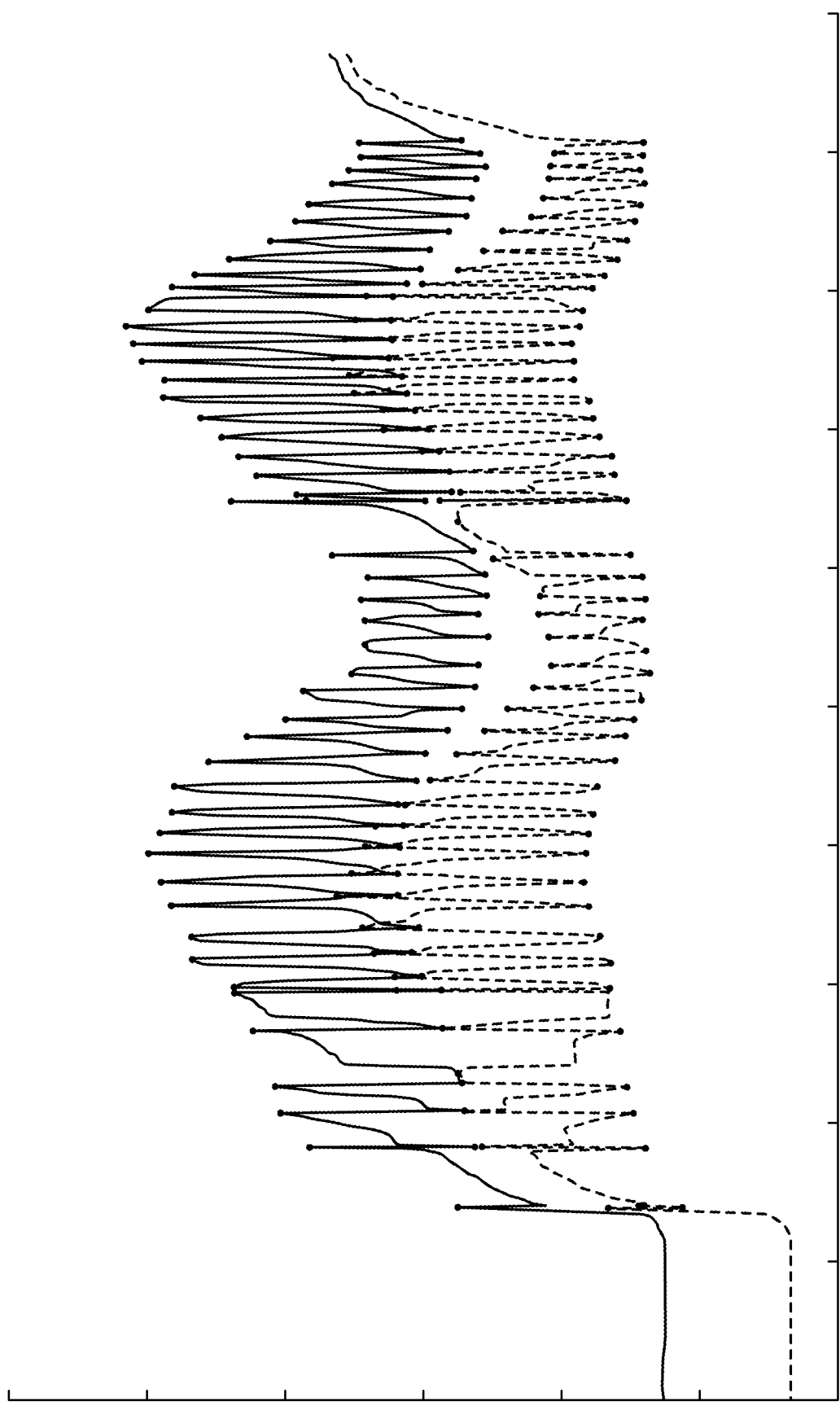
FIG. 30 shows the course of signal voltages generated by two optical sensors of a sensor arrangement during movement of a movable dosage programming component relative to the sensor arrangement according to an embodiment.

FIG. 30 shows the typical course of the signal voltages generated by two optical sensors, which may have a different gain profile to each other. The signal voltages are amplitude modulated. The different gain profiles may lead to significantly different signal voltages being generated by the two optical sensors and sent to a processor for processing the signal voltages. The different gain profiles may be for example due to tolerances associated with electronic components.

All of the algorithms pertain to a system with two optical sensors being arranged with a 180° phase shift so that the signal voltages generated by both sensors are anti-phase.

Figure 31:
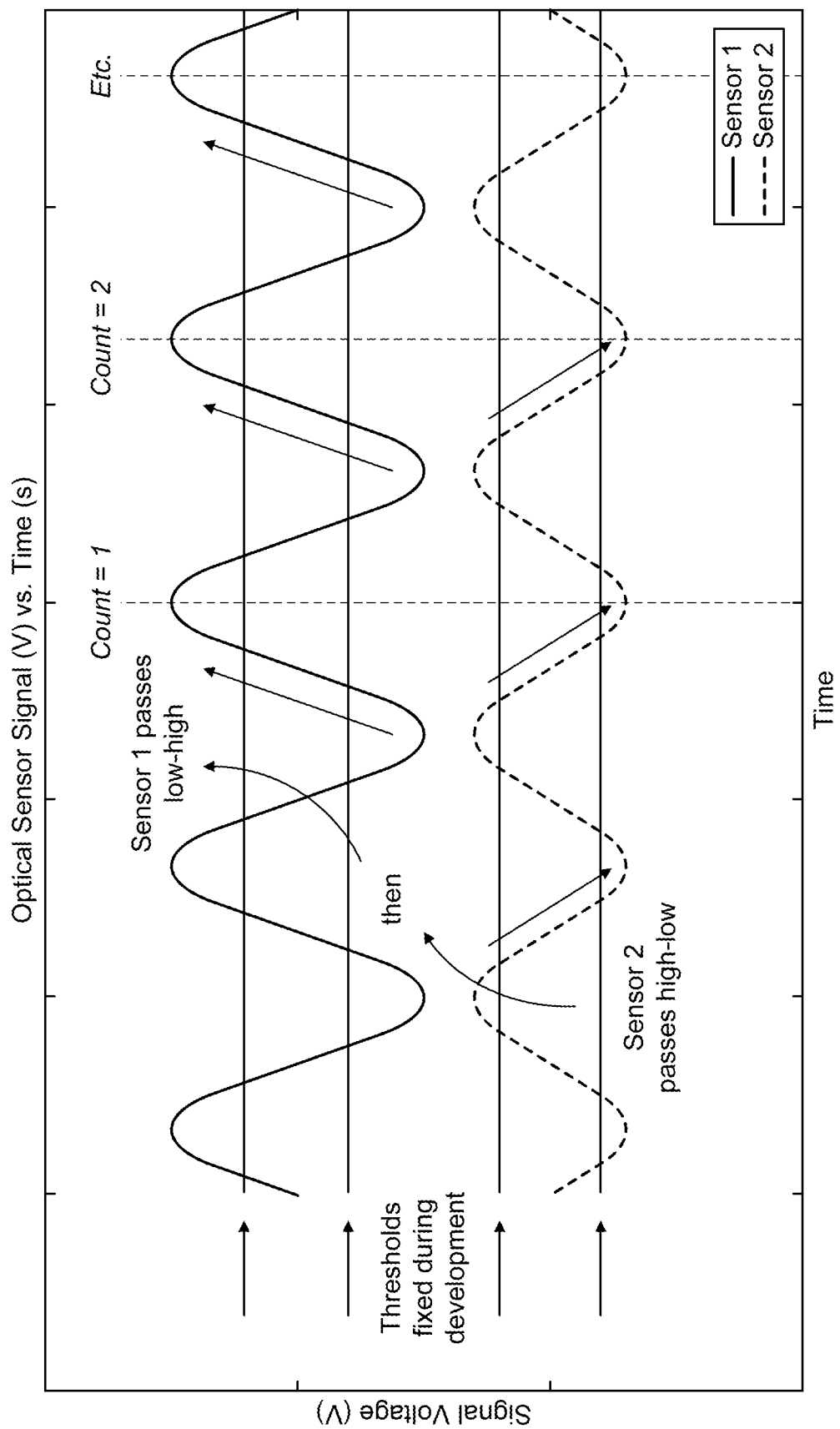
FIG. 31 shows the course of signal voltages generated by two optical sensors of a sensor arrangement during movement of a movable dosage programming component relative to the sensor arrangement and the setting of a "high" and "low" static threshold voltage for the signal voltages of each optical sensor of a sensor arrangement according to an embodiment of a first algorithm.

A first embodiment of an algorithm applies static thresholding: the algorithm sets a high threshold and a low threshold for the signal voltage of the first sensor and for the signal voltage of the second sensor, respectively; a unit of a dose selected with a movable dosage programming component is then counted if the signal voltage of the second sensor passes the high threshold and thereafter passes the low threshold, followed by the signal voltage of the first sensor passing the low threshold and thereafter passing the high threshold. During manufacture, a set of calibration geometry may be passed beneath each sensor at controlled distances to define the high and low thresholds. The thresholds are set for life such that the high threshold is always below the largest signal voltage observed during calibration (typically at minimum distance of substrate to sensor) and the low threshold is always below the smallest signal voltage observed during calibration (typically at maximum distance of substrate to sensor). The set thresholds for signal voltage of the first sensor and of the second sensor are shown in FIG. 31, which represents the course of the signal voltages of the first and second sensor. The unit counting is represented by the arrows.

Figure 32:
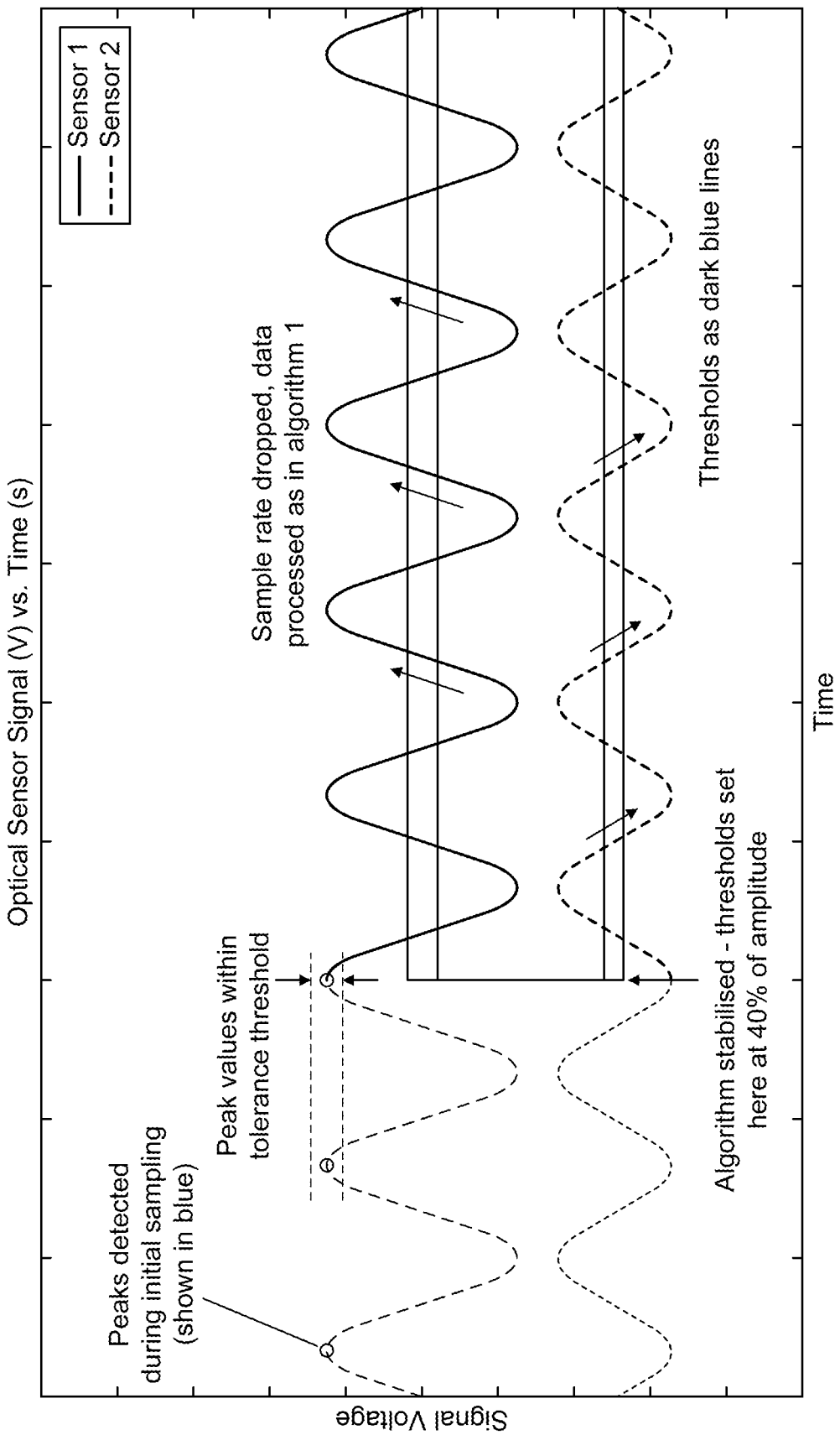
FIG. 32 shows the course of signal voltages generated by two optical sensors of a sensor arrangement during movement of a movable dosage programming component relative to the sensor arrangement and the setting of a "high" and "low" dynamic threshold voltage for the signal voltages of each optical sensor of a sensor arrangement according to an embodiment of a second algorithm.

A second embodiment of an algorithm applies dynamic thresholding: also this algorithm sets a high threshold and a low threshold for the signal voltage of the first sensor and for the signal voltage of the second sensor, respectively; a unit of a dose selected with a movable dosage programming component is then counted if the signal voltage of the second sensor passes the high threshold and thereafter passes the low threshold, followed by the signal voltage of the first sensor passing the low threshold and thereafter passing the high threshold. The thresholds may with this algorithm determined during the first few units delivered from each dose. As a dose is delivered, a sampling frequency for sampling the signal voltages of both sensors is set to a level higher than a sampling frequency used for normal operation and the signal voltages are sampled with the higher sampling frequency during delivery of a dose. Then, the magnitudes of at least two consecutive peak-throughs of the signal voltages of each sensor are determined with a peak-detection algorithm. If the determined magnitudes of at least two consecutive peak-throughs are within a predetermined tolerance signal range, for example a factory-set voltage tolerance, the high threshold and the low threshold for each signal voltage are then defined based upon a percentage of the measured peak and through signal voltage values or the determined magnitudes of at least two consecutive peak-throughs. This dynamic thresholding is undertaken for both sensors. Once the thresholds have been set, the sampling rate or frequency is reduced to a lower level typically used for normal operation, as peak detection is no longer required. This reduces power consumption of the algorithm. FIG. 32 demonstrates the dynamic thresholding by means of the course of the signal voltages of the first and second sensor.

Figure 33:
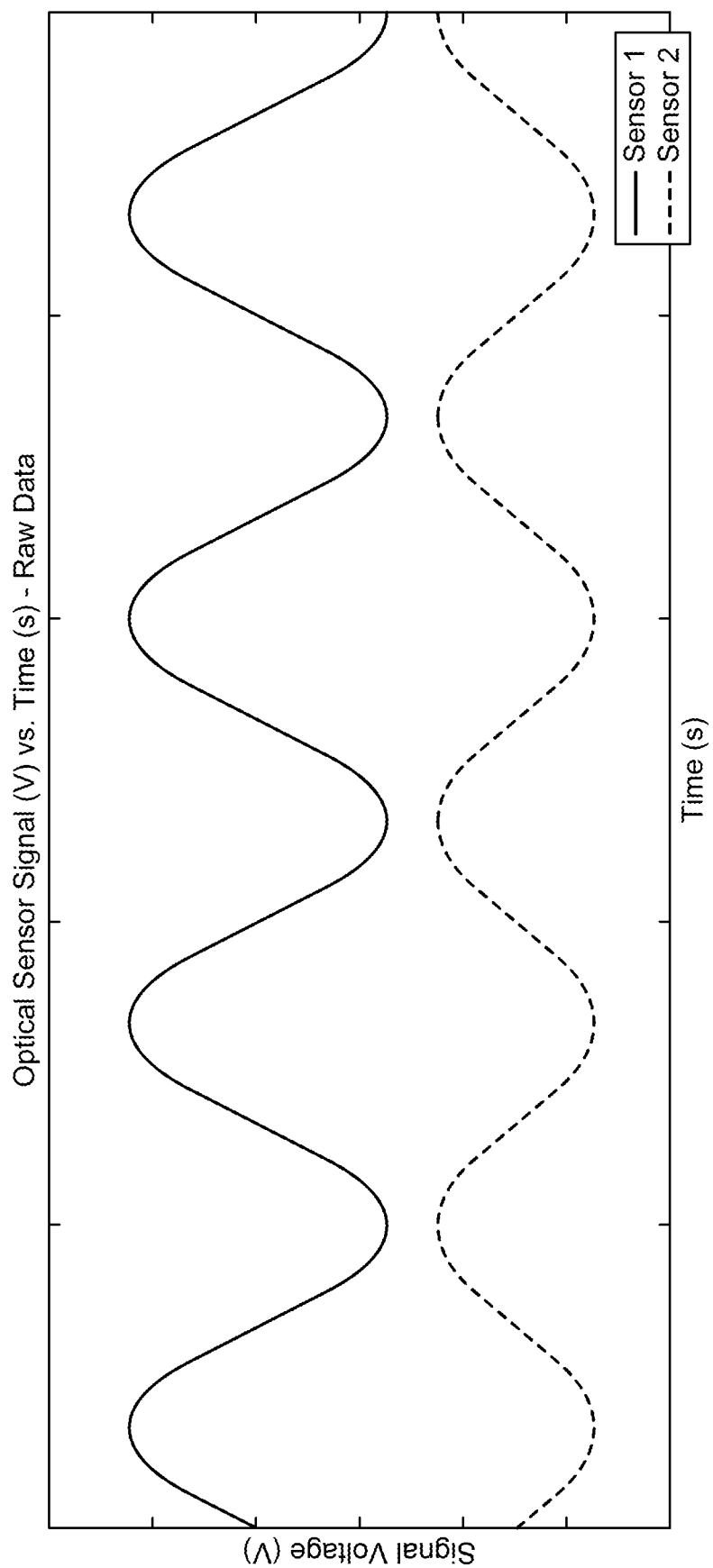
FIG. 33 shows the course of signal voltages generated by two optical sensors of a sensor arrangement that are typically not matched in terms of mean voltage and voltage amplitude.
Figure 34:
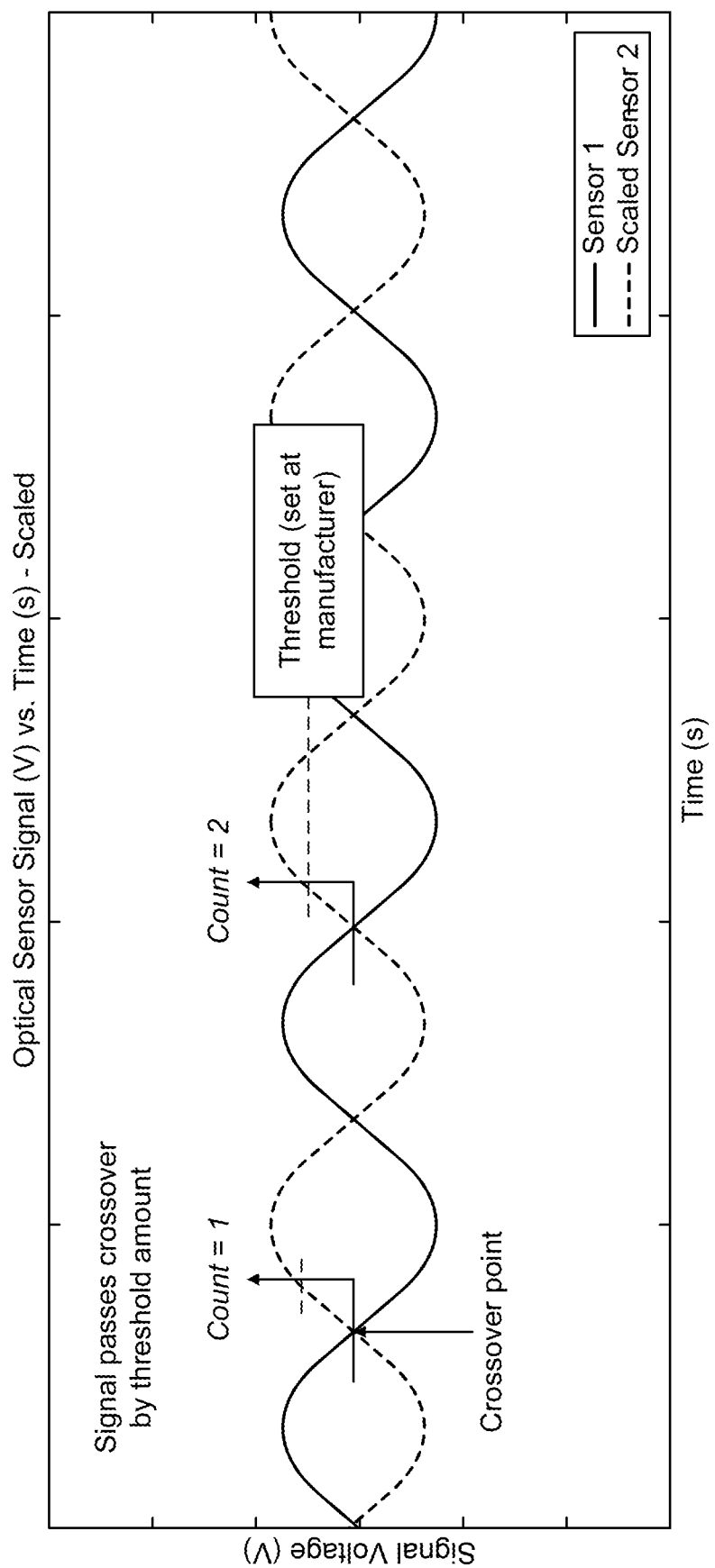
FIG. 34 shows the course of signal voltages generated by two optical sensors of a sensor arrangement during movement of a movable dosage programming component relative to the sensor arrangement and the detecting of a crossover point of the signal voltages of each optical sensor of a sensor arrangement according to an embodiment of a third algorithm.

A third embodiment of an algorithm does not rely on the setting of thresholds to detect low-high transitions, but rather counts a unit at the point when the voltage from the second sensor becomes greater than the voltage from the first sensor by a defined amount, i.e. the crossover point between the two sensor voltage signals. A unit is counted after the signals of the two optical sensors cross over in one direction, and subsequent units cannot be counted until the signals have crossed over at least once in the opposite direction. This effectively creates a flip-flop latch system. The signals may not deem to have "crossed over" until the difference between the signals, particularly the voltage difference between them exceeds a threshold value, which may be set during manufacture. For application of this algorithm, the signals from the two sensors should be matched in terms of mean voltage and mean amplitude. Since the signals from the two sensors are typically not matched in terms of mean voltage and voltage amplitude, as shown by the course of the two sensor signals in FIG. 33, they should be matched by scaling. As such, during manufacture, a set of calibration geometry is passed beneath each sensor at controlled distance and scaling factors for mean and amplitude are applied to the second sensor to match the mean and amplitude of its signal to the mean and amplitude of the signal of the first sensor. Once, the signals are scaled, the flip-flop dose counting algorithm can be used to count doses, as illustrated in FIG. 34.

A fourth embodiment of an algorithm is essentially identical to the third embodiment except that the scaling factors defined to give a common mean and amplitude for the two sensor signals may be calculated after each dose, removing the requirement to "factory set" these parameters during manufacture. In order to achieve this, the whole dataset for the signals of both sensors is stored, for example buffered in a memory, and the scaling factors are retrospectively calculated from the stored dataset in order to obtain a common mean and amplitude between the signals of both sensors. Once the scaling factors have been applied, this algorithm is deployed as before such that a unit is counted after the signals cross over in one direction, and subsequent units cannot be counted until the signals have crossed over at least once in the opposite direction.

Figure 35:
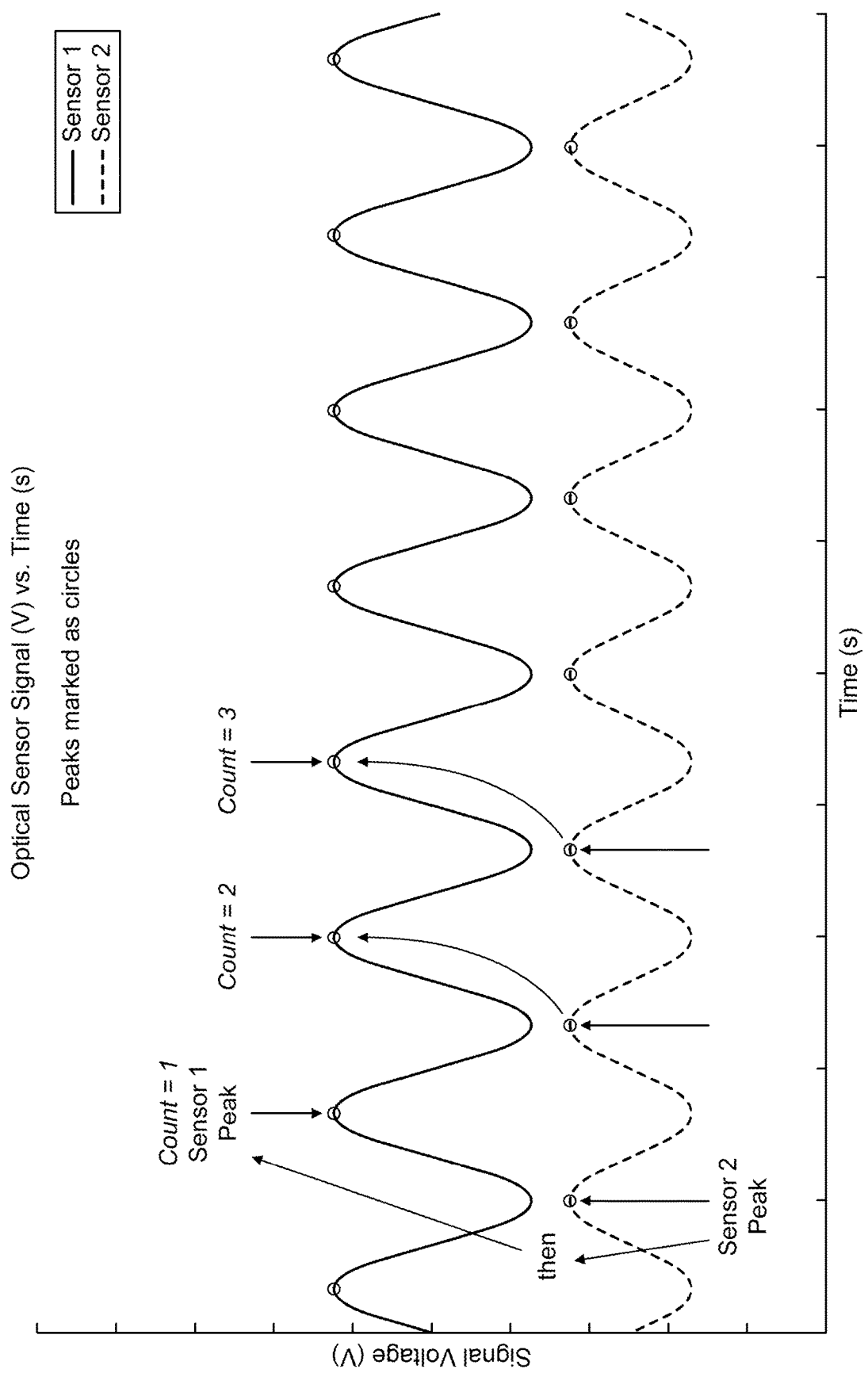
FIG. 35 shows the course of signal voltages generated by two optical sensors of a sensor arrangement during movement of a movable dosage programming component relative to the sensor arrangement and the detecting of a low power peak of the signal voltages of each optical sensor of a sensor arrangement according to an embodiment of a fifth algorithm.

A fifth embodiment of an algorithm does not rely on the setting of thresholds to detect low-high transitions, or the scaling of signals to match mean and amplitude, but rather uses a low power peak-detect method. A high sampling rate is not required, as the exact voltage value of the peak is not required, just the detection that a peak has occurred, i.e. a point of inflection on the voltage signal of a sensor. A flip-flop latch system may be employed as in other algorithms described herein in that a unit is counted when a peak is registered on the signal from the first sensor of two sensors, but subsequent units cannot be counted until at least one peak has been observed on the signal of the second sensor. This is illustrated in FIG. 35. This algorithm does not require scaling or factory setting of thresholds, which makes it robust to coping with tolerance variations and amplitude variations in use. It is also expected to be low power due to low computational complexity and the potential for a low power sampling rate than alternative algorithms.

The above described algorithms may permit low sampling frequencies and minimum computational complexity, while accommodating device-to-device tolerance variations, and in-use signal amplitude variations driven by a variable axial position of the sensor relative to a rotating number sleeve, particularly teeth or castellations of the sleeve.

Figure 36:
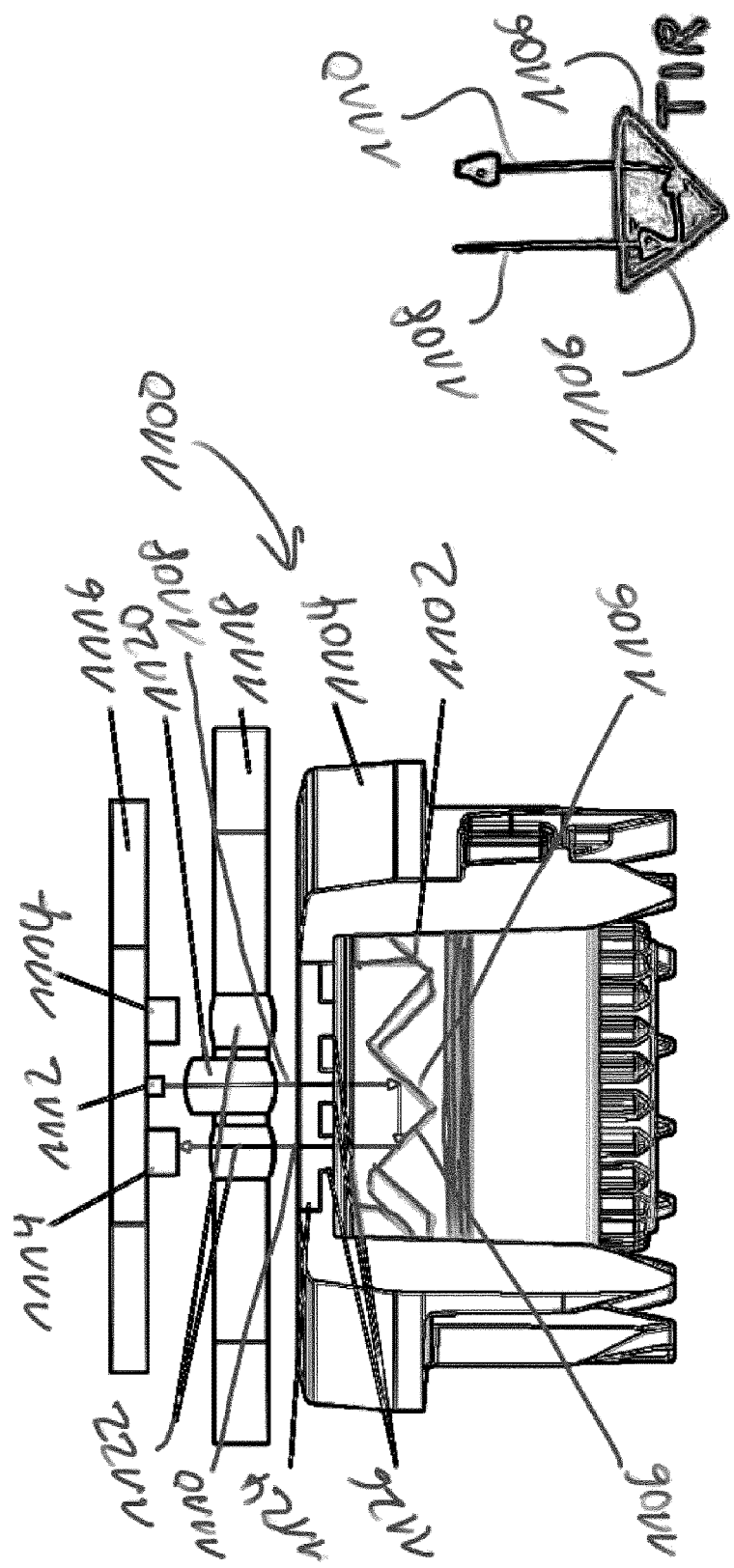
FIG. 36 shows a partial cross-sectional side view of a proximal end of an injection device according to a third embodiment.

A yet further embodiment of an injection device comprising a rotary encoder system 1100 having a predefined angular periodicity and an encoder ring or wheel 1102 is shown in FIG. 36. This embodiment can be used as counter for rotations, particularly for dose selection with an injection pen. The encoder ring 1102 may be arranged within an injection button 1104 of an injection device.

The encoder ring 1102 comprises a plurality of light reflectors arranged circumferentially around the encoder ring 1102 with a predefined periodicity. The light reflectors are arranged on the axial face side of the encoder ring so that light directed towards the light reflectors in an axial direction of the rotary encoder system 1100 may be received and reflected. Each light reflector comprises two reflecting surfaces 1106 arranged perpendicular to each other. Thus, incident light 1108 may be reflected from one reflecting surface to the other reflecting surface and from the other reflecting surface back to the source of the incident light by means of a total internal reflection (TIR) as shown in the right picture of FIG. 36.

At least the part of the encoder ring 1102 may be made of a transparent material, and the reflecting surfaces 1106 may be high-polished in order to reflect an amount of incident light back, which may generate a signal amplitude suitable for further processing.

A LED 1112 may be used as light source and two photodiodes 1114 for detecting the reflected light. The LED 1112 and the photodiodes 1114 may be arranged on a PCB 1116 of an electronic module for the injection device, which may also comprise electronic for controlling the light emission by the LED 1112 and process the output signals of the photodiodes 1114 in order to detect a rotation of either the PCB 1116 or the encoder ring 1102.

A housing 1118 may be provided for the PCB 1116, for example when the electronics is comprised by an add-on device for an injection pen. In order to allow a passing of light through the housing 1118 it may comprise an integrated lens 1120 for passing through the light emitted by the LED 1112 and lenses 1122 arranged before the photodiodes 1114 for letting reflected light pass through to the photodiodes 1114. The lens 1120 may be adapted to focus the light beams emitted by the LED 1112 on the reflecting surfaces 1106 of the light reflectors, and the lenses 1122 may be adapted to focus the light reflected back from the surfaces 1106 on light sensitive areas of the photodiodes 1114.

The button 1104 may comprise a window 1124 being made from a light transparent material and apertures 1126 for light emitted by the LED 1112 and reflected back from the surface 1106 to the photodiodes 1114. The light emitting and returning path is split by the TIR of the reflecting surfaces 1106 on the apertures 1126, which are placed side by side.

Figure 37:
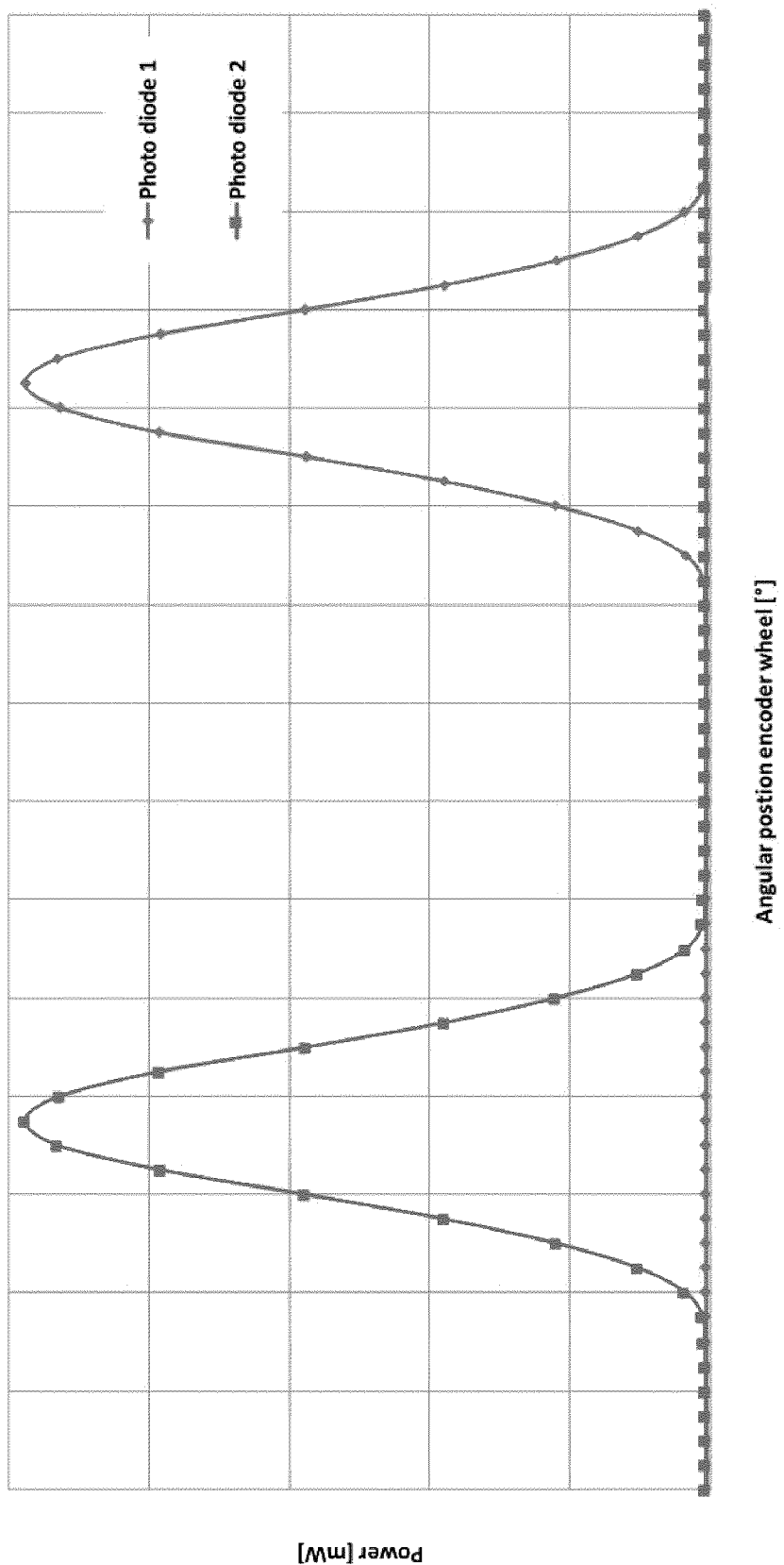
FIG. 37 shows the course of signal voltages generated by two optical sensors of a sensor arrangement during movement of a movable dosage programming component relative to the sensor arrangement according to the third embodiment of the injection device.

Simulations of the above described encoder concept have shown a good optical system performance with a relatively high peak irradiance, as shown in FIG. 37, which represents the power of two typical output signals of the photodiodes 1114. Also, the simulations have shown a relatively high signal-to-noise ratio, and, thus, showing a robust behaviour.

While the embodiments above have been described in relation to collecting data from an insulin injector pen, it is noted that embodiments of the disclosure may be used for other purposes, such as monitoring of injections of other medicaments.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentade-canoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An injection device comprising:
 a movable dosage programming component comprising a rotary encoder system having a predefined angular periodicity;
 a sensor arrangement comprising:
 a first optical sensor configured to detect a movement of the movable dosage programming component relative to the sensor arrangement during dosing of a medicament, wherein the first optical sensor is configured to operate in a strobe-sampling mode along a first time series of strobe pulses, and
 a second optical sensor configured to detect a rotary encoder system movement of the rotary encoder system relative to the second optical sensor, wherein the second optical sensor is configured to operate in a strobe-sampling mode along a second time series of strobe pulses, the first time series and second time series having a pulse density per time unit or a relative pulse phase varying according to a kinematical state of a dose programming component; and
 a processor arrangement configured to, based on the movement of the movable dosage programming component or the rotary encoder system movement, determine a medicament dosage administered by the injection device.

2. The injection device of claim 1, wherein the rotary encoder system is configured to be rotatable with respect to the first optical sensor during a dialing mode of operation of the injection device.

3. The injection device of claim 1, wherein the rotary encoder system comprises an encoder ring comprising a plurality of substantially light reflective flags arranged circumferentially around the encoder ring in accordance with the predefined angular periodicity.

4. The injection device of claim 3, wherein the encoder ring comprises a plurality of substantially light absorbent flags arranged to alternate with the plurality of substantially light reflective flags in accordance with the predefined angular periodicity.

5. The injection device of claim 3, wherein lateral edges of the plurality of substantially light reflective flags are inwardly inclined.

6. The injection device of claim 1, wherein the second optical sensor is configured to operate in a strobe-sampling mode at a second frequency lower than a first frequency.

7. The injection device of claim 6, wherein the first and second optical sensors have an angular offset equal to half the predefined angular periodicity, and wherein the first and second optical sensors are configured to operate in a synchronous mode of operation.

8. The injection device of claim 6, wherein the first and second optical sensors have an angular offset that differs from half the predefined angular periodicity, and wherein the first and second optical sensors are configured to operate in a staggered mode of operation with an offset time between sampling by the first and second optical sensors.

9. The injection device of claim 8, wherein the angular offset is less than half the predefined angular periodicity.

10. The injection device of claim 8, wherein the offset time is varied based on a relative rotational speed of the rotary encoder system with respect to the first and second optical sensors.

11. The injection device of claim 10, wherein the offset time is decreased in response to an increase in the relative rotational speed.

12. The injection device of claim 1, further comprising an injection button and an electrical switch connected to the sensor arrangement, the electrical switch arranged to supply power to the sensor arrangement in response to actuation of the injection button.

13. The injection device of claim 1, further comprising a medicament containing cartridge.

14. A module configured to be used with or applied to an injection device comprising a movable dosage programming component with a rotary encoder system, the module comprising:
 a sensor arrangement comprising at least one optical sensor being configured to detect movement of the movable dosage programming component of the injection device relative to the sensor arrangement during dosing of a medicament and a collimating optics being arranged between the at least one optical sensor and the movable dosage programming component, wherein the at least one optical sensor is configured to operate in a strobe-sampling mode along a time series of strobe pulses, the time series having a pulse density per time unit or a relative pulse phase varying according to a kinematical state of a dose programming component; and
 a processor arrangement configured to, based on the movement of the movable dosage programming component, determine a medicament dosage administered by the injection device.

15. The module of claim 14, wherein the collimating optics comprises one or more of:
 one or more discrete collimating lenses; and
 one or more light pipes.

16. The module of claim 15, wherein a discrete collimating lens is arranged between each optical sensor and each light pipe, between each light pipe and the movable dosage programming component, or between each optical sensor and each light pipe and between each light pipe and the movable dosage programming component.

17. The module of claim 16, wherein a single discrete collimating lens is provided for each sensor and is configured to cover a transmitter portion of the sensor, a receiver portion of the sensor, or a transmitter and a receiver portion of the sensor, and wherein the single discrete collimating lens is a lens array covering the sensor.

18. A method for processing signals generated by a sensor arrangement of an injection device or a module, which comprises a sensor arrangement with two optical sensors arranged at 180° wherein a first signal of the first sensor of the two sensors and a second signal of the second sensor of the two sensors are in anti-phase, and wherein at least one of the two optical sensors is configured to operate in a strobe-sampling mode along a time series of strobe pulses, the time series having a pulse density per time unit or a relative pulse phase varying according to a kinematical state of a dose programming component, the method comprising the steps of:

setting a high threshold and a low threshold for the first signal of the first sensor and for the second signal of the second sensor, respectively; and counting a unit of a dose selected with a movable dosage programming component of the injection device or the module when the second signal of the second sensor passes the high threshold and thereafter passes the low threshold, and thereafter the first signal of the first sensor passes the low threshold and thereafter passes the high threshold.

19. The method of claim 18, the step of setting a high threshold and a low threshold for the first signal of the first sensor and for the second signal of the second sensor, respectively, comprises a calibration step performed during manufacturing of the module for setting the high and low thresholds, wherein the calibration step comprises:

passing a set of calibration geometry beneath each sensor at controlled distances for calibration, and setting the high and low thresholds such that the high threshold is always below a largest signal level of a respective sensor signal observed during calibration and the low threshold is always below a smallest signal level observed during calibration.

20. The method of claim 18, the step of setting a high threshold and a low threshold for the first signal of the first sensor and for the second signal of the second sensor, respectively, comprises the steps of:

setting a sampling frequency for sampling the signals of both sensors to a level higher than a sampling frequency used for normal operation and sampling the signals during delivery of a dose with an injection device comprising the module, determining magnitudes of at least two consecutive peak-throughs of a respective signal of each sensor, and setting the high threshold and the low threshold for each signal to a percentage of the magnitudes of at least two consecutive peak-throughs if the magnitudes of at least two consecutive peak-throughs are within a predetermined tolerance signal range.

* * * * *